United States Patent
Pei et al.

(10) Patent No.: US 9,163,217 B2
(45) Date of Patent: *Oct. 20, 2015

(54) METHOD FOR INCREASING THE EFFICIENCY OF INDUCING PLURIPOTENT STEM CELLS

(75) Inventors: Duanqing Pei, Guangdong (CN); Tao Wang, Guangdong (CN)

(73) Assignee: GUANGZHOU INSTITTUTES OF BIOMEDICINE AND HEALTH, CHINESE ACADEMY OF SCIENCES, Guangzhou (CN)

( * ) Notice: Subject to any disclaimer, the term of this patent is extended or adjusted under 35 U.S.C. 154(b) by 46 days.

This patent is subject to a terminal disclaimer.

(21) Appl. No.: 13/808,596

(22) PCT Filed: Mar. 31, 2012

(86) PCT No.: PCT/CN2012/073375
§ 371 (c)(1),
(2), (4) Date: Jan. 6, 2013

(87) PCT Pub. No.: WO2013/056535
PCT Pub. Date: Apr. 25, 2013

(65) Prior Publication Data
US 2013/0302893 A1  Nov. 14, 2013

(30) Foreign Application Priority Data
Oct. 21, 2011  (CN) .......................... 2011 1 0323779

(51) Int. Cl.
*C12N 15/00* (2006.01)
*C12N 5/0775* (2010.01)
*C12N 5/074* (2010.01)

(52) U.S. Cl.
CPC ............ *C12N 5/0662* (2013.01); *C12N 5/0696* (2013.01); *C12N 2500/38* (2013.01); *C12N 2501/602* (2013.01); *C12N 2501/72* (2013.01); *C12N 2506/13* (2013.01); *C12N 2510/00* (2013.01)

(58) Field of Classification Search
None
See application file for complete search history.

(56) References Cited

U.S. PATENT DOCUMENTS

| 2009/0269763 A1 | 10/2009 | Eilertsen et al. |
| 2009/0275032 A1 | 11/2009 | Eilertsen et al. |
| 2011/0136145 A1* | 6/2011 | Song et al. .................... 435/7.21 |
| 2012/0295351 A1* | 11/2012 | Sherley .......................... 435/377 |

FOREIGN PATENT DOCUMENTS

| WO | WO2010108126 A2 | 9/2010 |
| WO | WO 2010108126 A2 * | 9/2010 |
| WO | WO2011051264 A2 | 5/2011 |

OTHER PUBLICATIONS

Furue et al. "Development of defined medium for mouse, monkey and human ES cell culture." Japanese Society for Alternatives to Animal Experiments (2008); AATEX 14, Special Issue, pp. 601-603.*

Miyamoto et al. "Human Placenta Feeder Layers Support Undifferentiated Growth of Primate Embryonic Stem Cells." Stem Cells (2004);22: pp. 433-440.*

Takahashi et al. "Induction of Pluripotent Stem Cells from Mouse Embryonic and Adult Fibroblast Cultures by Defined Factors." Cell (2006); 126: pp. 663-676.*

Chen et al. "Role of MEF feeder cells in direct reprogramming of mouse tail-tip fibroblasts." Cell Biology International (2009); 33: pp. 1268-1273.*

Esteban et al. "Vitamin C enhances the generation of mouse and human induced pluripotent stem cells." Cell Stem Cell. (Jan. 2010, E-published Dec. 2009); 6(1): pp. 71-79.*

Takahashi et al. "Induction of Pluripotent Stem Cells from Mouse Embryonic and Adult Fibroblast Cultures by Defined Factors." Cell (Aug. 2006); 126 (4):pp. 663-676.*

Esteban et al. "Vitamin C enhances the generation of mouse and human induced pluripotent stem cells." Cell Stem Cell. Jan. 8, 2010;6(1):71-9.*

Djuric and Ellis. "Epigenetics of induced pluripotency, the seven-headed dragon."Stem Cell Res Ther. Mar. 15, 2010;1(1):3.*

Takahashi et al. "Induction of pluripotent stem cells from mouse embryonic and adult fibroblast cultures by defined factors." Cell. Aug. 25, 2006;126(4):663-76. Epub Aug. 10, 2006.*

Huangfu et al. (a). "Induction of pluripotent stem cells by defined factors is greatly improve"Nat Biotechnol. Jul. 2008;26(7):795-7. Epub Jun. 22, 2008.*

Huangfu et al. (b). "Induction of pluripotent stem cells from primary human fibroblasts "Nat Biotechnol. Nov. 2008;26(11):1269-75. Epub Oct. 12, 2008.*

Yamanaka, S. "Induction of pluripotent stem cells from mouse fibroblasts by four transcription factors." Cell Prolif. Feb. 2008;41 Suppl 1:51-6.*

Zhang et al. "Efficient generation of fully reprogrammed human iPS cells via po" PLoS One. 2011;6(10):e26592. Epub Oct. 26, 2011.*

* cited by examiner

Primary Examiner — Thaian N Ton
Assistant Examiner — Titilayo Moloye

(57) ABSTRACT

The present invention relates to a method for increasing the efficiency of inducing pluripotent stem cells by utilizing genes Jhdm1b and Jhdm1a that modify histone. By utilizing Jhdm1b, Jhdm1a, and a stem cell inducing factor, the present invention increases the efficiency of inducing pluripotent stem cells and increases the quality of induced pluripotent stem cells. The stem cell inducing factor is a combination of Oct4 and Klf4, or a combination of Sox2, Oct4, and Klf4, or a combination of Oct4 and Sox2, and Oct4 alone. The method further comprises exposing the cells to vitamin C, which further increases the efficiency of inducing pluripotent stem cells as compared with the case where no vitamin C is used. By using less stem cell reducing factors, the method of the present invention reduces the potential carcinogenicity, obtains a high inducing efficiency, and provides high-quality induced pluripotent stem cells capable of germ-line transmission.

8 Claims, 7 Drawing Sheets

METHOD FOR INCREASING THE EFFICIENCY OF INDUCING PLURIPOTENT STEM CELLS

SEQUENCE LISTING

A substitute Sequence Listing, incorporated by reference in its entirety, is provided on identical compact discs (labeled Copy 1 Replacement 07/19/2013, Copy 2 Replacement 07/19/2013, and Computer-readable form Replacement 07/19/2013), each compact disc containing the file 130718_VM41838_PW12048-seq listing-amended-JH.txt, created on Jul. 18, 2013, and is 31.4 KB in size.

BACKGROUND OF THE INVENTION

The present invention relates to a method for increasing the efficiency of inducing pluripotent stem cells, and more particularly, to a method for increasing the efficiency of inducing pluripotent stem cells by utilizing genes Jhdm1b and Jhdm1a that modify histone.

China is a populous country in the world and also has the highest number of organ losses, damages, failures, and functional disorders as a result of trauma, disease, aging, and heredity. Classical medical therapies based on drugs and surgeries have failed to satisfy the tremendous demand of clinical medicine. As a result, the research on the stem cells and the regenerative medicine attracts the attention of numerous research entities and all sectors of the society.

The cell transplantation therapy constitutes an important research direction of the regenerative medicine, and specific types of cell transplantations may be used to treat heart injury, nervous system degenerative diseases, spinal injury, renal failure, hematological system diseases, and so on. However, the cell transplantation therapy is facing many intricate problems such as allograft rejection and limited cell sources.

The stem cell is a type of cell capable of selfrenewal and can differentiate into various functional cells under certain conditions. Based on their development stage, the stem cells are divided into embryonic stem cells and adult stem cells. Based on their development potential, the stem cells are divided into three types: totipotent stem cells, pluripotent stem cells, and unipotent stem cells. The stem cell is a type of immature cell that is not fully differentiated and has a potential function to regenerate various tissues and organs and the human body, so it is called "universal cell" in the field of medicine.

In order to solve the problems encountered by the cell transplantation therapy, the transformation of cell fate attracts the attention of more and more scientists. Although the determination of cell differentiation and fate has always been considered as an irreversible and stable process in the development process, there are more and more in vitro evidences showing that this process is reversible.

The study on regulation of cell fate is just in a laboratory investigation state and is far from clinical trial. These transformed cells obtained through over-expression of transcription factors still have many application problems, for example, viral sequences integration, potential oncogenicity, the purity of the resultant transdifferentiated cells, and whether they can make up for normal cells which are damaged in certain conditions and play their due roles in the organism.

The induced pluripotent stem cell (iPS) is a type of cell that resembles with embryonic stem cell and has development totipotency. It acquires the properties of the stem cell by inducing the somatic cell through introducing specific ES enriched genes. In 2006, Japanese scientist Yamanaka introduced 24 candidate genes into mouse fibroblasts by using a retrovirus based vector, screened FBX15 positive cells by means of G418 resistance to isolate iPS clones similar to embryonic stem cells, and finally identified that 4 factors including Oct3/4, Sox2, c-Myc, and Klf4 are sufficient to induce mouse FBX15-iPS cells; as compared with embryonic stem cells, these cells are similar with embryonic stem cells in the aspects of clone shape, proliferation capability and ability to form teratoma, but they are different from embryonic stem cells in terms of gene expression and genomic methylation profile and cannot obtain living chimeric mice. Afterwards, this group and other two groups changed the screening method, and they used Nanog as the standard and obtained iPSs that are similar to embryonic stem cells in many aspects and these iPSs can produce chimeric offspring. Recently, the three research groups independently confirmed, by tetraploid complementation test, that mouse iPS cells can develop into an individual and possess development totipotency.

Following the method of inducing mouse iPSs, in 2007, each of the two groups Yamanaka [8] and Yu Junying [9] successfully reprogrammed human somatic cells into iPS cells, wherein the former transduced Oct3/4, Sox2, c-Myc, and Klf4 into human epidermal fibroblasts by using a retrovirus, while the latter incorporated Otc3/4, Sox2, Nanog, and Lin28 into foreskin cells by using a lentivirus. Both of the analysis on gene expression profiling and the analysis on the methylation of the promoter regions of genes Oct3/4 and Nanog showed that the human iPS cell line is very similar to the corresponding embryonic stem cell line, and all of the cells can develop into 3 germinal layers when they are injected into the body of a nude mouse. Furthermore, somatic cells can be successfully induced into iPSs in rat, swine, and monkey, in addition to mouse and human.

The cells that can be successfully reprogrammed are not only limited to fibroblasts, and many other types of adult cells can also be successfully induced into iPS cells, including pancreas beta cells, adult neural stem cells, hepatocytes, gastric cells, mature B cells, haematopoietic cells, meningocytes, adipose-derived stem cells, cord blood cells, peripheral blood CD34 positive cells, and keratinocytes. For cells at different differentiation stages, the difficulties in inducing and reprogramming them into iPSs are different. Take mouse haematopoietic cells as an example: the reprogramming efficiency of haematopoietic stem cells and haematopoietic progenitor cells may be up to 28% which is 300 times that of terminally differentiated T cells and B cells.

In inducing iPSs, it is often to incorporate an exogenous gene into cells by means of a retrovirus and a lentivirus, which provides very high gene transduction efficiency. However, integration of the viral sequence into the genome of the cell may result in gene insertional mutagenesis and even carcinogenicity, so this gene introduction method having potential risks is obviously unfavorable to application of the iPS technique in the field of regenerative medicine. Therefore, a different study group used non-integrating vectors to induce iPSs and succeeded. These vectors include an adenovirus vector, a common expression vector, a transposon, an episome vector, and a minicircle DNA vector.

Both of the combination of Sox2, Klf4, Oct3/4 and c-Myc and the combination of Sox2, Oct3/4, Nanog and Lin28 can successfully induce the generation of iPSs. Further studies found that c-Myc is not essential for reprogramming and the three transcription factors including Sox2, Klf4 and Oct3/4 are sufficient to drive the reprogramming of human and mouse somatic cells. Neural stem cells endogenously express high levels of Sox2, Klf4, and c-Myc, so it only needs to incorporate exogenous Oct3/4 in order to successfully induce iPSs. Among the transcription factors used in reprogramming, Sox2, Klf4, and c-Myc can all be replaced by other members of the same family, for example, Klf2 and Klf5 can replace Klf4; Sox1 and Sox3 can replace Sox2; N-Myc and L-Myc can replace c-Myc; but Oct1 and Oct6 cannot replace Oct4. Esrrb directly binds to Oct3/4 protein to regulate the self-regeneration and totipotency of stem cells, and in reprogramming, Esrrb can replace Klf4 to induce iPSs in combination with Sox 2 and Oct3/4. Oct3/4 is a very important transcription factor in reprogramming. Recent studies found that nuclear receptors LRH-1 (Nr5a2) and Nr5a1 can replace Oct3/4 and can induce mouse adult cells into iPSs in combination with Klf4 and Sox2.

However, so far, there are several different combinations of transcription factors capable of reprogramming, including Oct4, Klf4, Sox2, and c-Myc; Oct4, Nanog, Lin28, Sox2; Sox2, Klf4, and Lrh1; Oct4 and bmi1, as well as reprogramming-related genes such as esrrb and tbx3. For the transcription factor combinations required by existing reprogramming methods, it needs to incorporate as many as 3 or 4 transcription factors and the induction efficiency is low. How to reduce the number of transcription factors while maintaining a high reprogramming efficiency is of great importance for reducing the accumulation of cell mutations in reprogramming and for improving the operability of the reprogramming technique. Furthermore, searching for genes that replace common transcription factors facilitates the study of the reprogramming mechanism and the improvement of the reprogramming technique.

BRIEF SUMMARY OF THE INVENTION

An objective of the present invention is to provide a method of reducing the number of transcription factors while maintaining a high reprogramming efficiency, reducing the accumulation of cell mutations in reprogramming, and improving the operability of the reprogramming technique.

To achieve this objective, the following technical solution is adopted to provide a method for increasing the efficiency of inducing pluripotent stem cells, comprising the following steps:

a. transferring a transcription factor and Jhdm1b into mammalian adult cells which are then cultured in an inducing medium to induce pluripotent stem cell clones, wherein the transcription factor is Oct4 alone, or a combination of Oct4, Klf4, and Sox2, or a combination of Oct4, Klf4, c-Myc, and Sox2;

b. culturing and expanding the induced pluripotent stem cell clones in a stem cell culture medium.

Another technical solution of the present invention is to provide a method for increasing the efficiency of inducing pluripotent stem cells, comprising the following steps:

a. transferring a transcription factor and Jhdm1b into mammalian adult cells which are then cultured in an inducing medium containing vitamin C to induce pluripotent stem cell clones, wherein the transcription factor is Oct4 alone, or a combination of Oct4 and Sox2, or a combination of Oct4 and Klf4, or a combination of Oct4, Klf4, and Sox2, or a combination of Oct4, Klf4, Sox2, and c-Myc;

b. culturing and expanding the induced pluripotent stem cell clones in a stem cell culture medium.

Preferably, the above steps are as follows:

a. transferring a transcription factor and Jhdm1b into mammalian adult cells which are then cultured in an inducing medium to induce pluripotent stem cell clones, wherein the transcription factor is Oct4 alone, or a combination of Oct4 and Sox2, or a combination of Oct4 and Klf4, or a combination of Oct4, Klf4, and Sox2;

b. culturing and expanding the induced pluripotent stem cell clones in a stem cell culture medium.

Preferably, the transcription factor and Jhdm1b are encoded or noncoding RNAs, proteins, or polypeptides capable of inducing pluripotent stem cells.

Preferably, the transferring of Jhdm1b into mammalian adult cells is achieved by incorporating a vector capable of expressing Jhdm1b into the cells.

Preferably, the vector is a viral vector, a plasmid vector, an external satellite vector, or an mRNA vector, or is chemically synthesized directly.

Preferably, the viral vector is a retrovirus which is a pMXs vector.

Preferably, the Jhdm1b is a polypeptide for demethylation modification, a functional variant thereof, and a functional fragment thereof.

Preferably, the mammalian adult cells are fibroblasts, neural cells, haematopoietic cells, and neuroglial cells.

Preferably, the mammalian adult cells are mouse embryonic fibroblasts.

Another technical solution is provided by the present invention to provide a method for increasing the efficiency of inducing pluripotent stem cells, comprising the following steps:

a. transferring a transcription factor, Jhdm1b, and Jhdm1a into mammalian adult cells which are then cultured in an inducing medium to induce pluripotent stem cell clones, wherein the transcription factor is Oct4 alone, or a combination of Oct4 and Sox2, or a combination of Oct4 and Klf4, or a combination of Oct4, Klf4, and Sox2;

b. culturing and expanding the induced pluripotent stem cell clones in a stem cell culture medium.

Preferably, the above method comprises the following steps:

a. transferring a transcription factor, Jhdm1b, and Jhdm1a into mammalian adult cells which are then cultured in an inducing medium containing vitamin C to induce pluripotent stem cell clones, wherein the transcription factor is Oct4;

b. culturing and expanding the induced pluripotent stem cell clones in a stem cell culture medium containing vitamin C.

The beneficial effects of the present invention are as follows: by utilizing polypeptides Jhdm1b and Jhdm1a that modify histone, and a stem cell inducing factor, the present invention increases the efficiency of inducing pluripotent stem cells and increases the quality of induced pluripotent stem cells. The present method achieves better effects by using less types of stem cell inducing factors as compared with the existing methods of inducing pluripotent stem cells. Preferably, the method of the present invention uses Oct4, Klf4 and Sox2, Oct4 and Klf4, Oct4 and Sox2, or Oct4 alone. The method of the present invention further comprises exposing the cells to vitamin C, which further increases the efficiency of inducing pluripotent stem cells as compared with the case where no vitamin C is used. By using less stem cell reducing factors, the method of the present invention reduces the potential carcinogenicity, obtains a high inducing efficiency, and provides high-quality induced pluripotent stem cells capable of germ-line transmission.

DETAILED DESCRIPTION OF THE INVENTION

Figure 1:
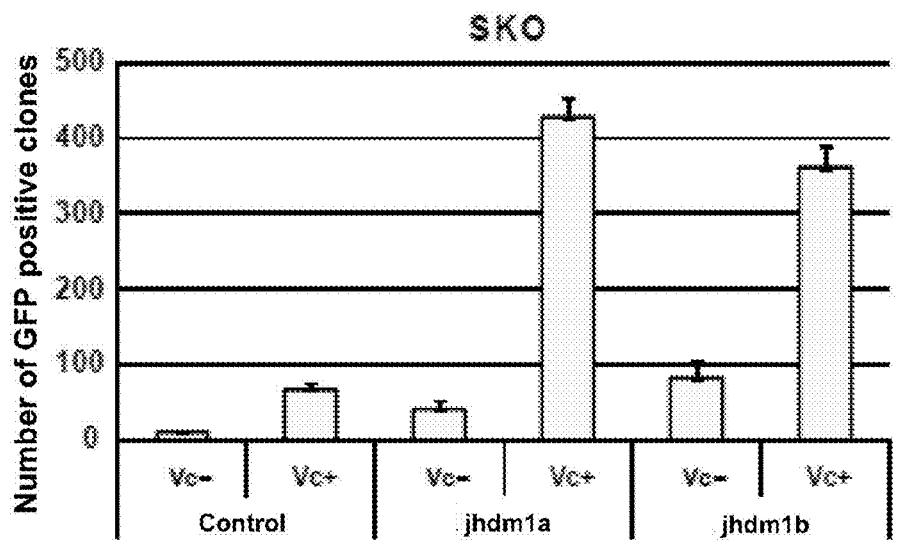
FIG. 1 shows data indicating that Jhdm1a or Jhdm1b increases the efficiency of inducing pluripotent stem cells as mediated by SKO, wherein the control is a pMXs-FLAG empty vector where no gene sequence is inserted.

All the technical terms used herein have the same meanings as understood by those of ordinary skills in the art. For the definitions and terms of the art, one killed may refer to, for example, Current Protocols in Molecular Biology, edited by Ausubel, et al, John Wiley & Sons, 2009. The abbreviations of amino acid residues are the standard 3-letters and/or 1-letter codes that are used in the art to represent one of the 20 common L-amino acids.

In spite of the numerical ranges and parameter approximations shown in the broad scope of the present invention, the values shown in the specific embodiments shall be recorded as accurate as possible. However, any values must contain certain error by themselves inevitably, which are attributable to their standard deviations present in their respective measurements. In addition, all the ranges disclosed herein shall be construed as covering any and all sub-ranges thereof.

The terms "polypeptide" and "protein" used herein may be used interchangeably to indicate a string of at least two amino acid residues that are interconnected with one another via covalent bond (e.g., peptide bond), which may be recombinant polypeptides, natural polypeptides, or synthetic polypeptides. Particularly, the polypeptides described herein are human and/or mouse polypeptides.

The terms "variant", "polypeptide variant" or "analogue" used herein indicates a polypeptide that is different from the original polypeptide in the amino acid sequence by one or more substitutions, deletions, insertions, fusions, truncations or any combinations thereof. The variant polypeptide may be fully functional or may lack one or more active functions. The term "functional variant" used herein only contains, for example, conservative changes or the changes in non-critical residues or non-critical regions, and retains the functions of the original polypeptide. The functional variant may further contain the substitution of similar amino acids, which results in unchanged functions or insignificant function changes. Amino acids that are important for the functions may be identified by methods known in the art, for example, site directed mutagenesis or glycine scanning mutagenesis (Cunningham, B. and Wells, J., Science, 244: 1081-1085, 1989). Sites that are crucial to polypeptide activity may be determined by, for example, structural analysis such as crystallization, nuclear magnetic resonance, or photoaffinity labeling (Smith, L. et al., J. Mol. Biol., 224: 899-904, 1992; de Vos, A. et al., Science, 255: 306-312, 1992).

In some embodiments of the present invention, the variants of Jhdm1a are selected from polypeptides comprising an amino acid sequence that is at least 70% (preferably 80%, 90%, 95%, 98%, and 99%) homologous to the amino acid sequence encoded by SEQ ID NO: 1. In other embodiments of the present invention, the variants of Jhdm1b are selected from polypeptides comprising an amino acid sequence that is at least 70% (preferably 80%, 90%, 95%, 98%, and 99%) homologous to the amino acid sequence encoded by SEQ ID NO: 2. The amino acid sequence encoded by Jhdm1a is SEQ ID NO: 7, and the amino acid sequence encoded by Jhdm1b is SEQ ID NO: 8.

The term "fragment" used herein refers to a molecule that is only a part of a full-length sequence. For example, a Jhdm1b polypeptide fragment is truncated Jhdm1b. The fragments may contain a sequence from any end of the full-length sequence or a sequence from the middle of the full-length sequence. The fragment may be a "functional fragment", for example, a fragment that retains one or more functions of the full-length polypeptide. The term "functional fragment" used herein indicates that said fragment retains the functions of the full-length polypeptide, for example, inducing pluripotent stem cells or increasing the efficiency of inducing pluripotent stem cells.

Unless otherwise stated, when polypeptides, nucleic acids, or other molecules are mentioned herein, they include functional variants and functional fragments. For example, Jhdm1b and Jhdm1a further indicate the functional variants and functional fragments of natural Jhdm1b and Jhdm1a respectively.

The term "Jhdm1b" used herein may indicate a member of the family of JmjC-domain-containing histone demethylase (JHDM) that is evolutionarily conserved and widely expressed. It is also called Fbx110. In particular, said polypeptide is a human and/or mouse polypeptide.

The term "Jhdm1a" used herein may indicate another member of the family of JmjC-domain-containing histone demethylase (JHDM). It is also called Fbx111. In particular, said polypeptide is a human and/or mouse polypeptide.

The term "induced pluripotent stem cells" or "iPSs" used herein may be used interchangeably to indicate pluripotent stem cells obtained by artificially inducing non-pluripotent cells (such as somatic cells). Said inducing is generally achieved by forced expression of a specific gene, and this process is also called "inducing cells into pluripotent stem cells" herein.

The term "stem cell inducing factor" used herein indicates a factor that is capable of inducing cells into pluripotent stem cells by itself alone or in combination with other factors, such as proteins, polypeptides, and encoded or noncoding RNAs. Preferably, the stem cell inducing factor is a transcription factor, including Oct-3/4, the members of Sox family, the members of Klf family, the members of Myc family, Nanog, LIN28 and the like. Preferably, the stem cell inducing factor is selected from one or more of Oct4, Klf4, Sox2, and c-myc. More preferably, the stem cell inducing factor includes at least Oct4. In particular, the polypeptide is a human and/or mouse polypeptide.

The term "Oct4" used herein indicates a member of the family of octamer transcription factors. It plays a crucial role in maintaining the pluripotency of the cells. In the literatures, Oct4 was also called Oct3.

The term "Klf4" used herein indicates a member of the KrOppel-like family of transcription factors.

The term "Sox2" used herein indicates a member of the family of Sox transcription factors.

The term "c-myc" used herein indicates a transcription factor that is well known by those skilled in the art. It regulates the expression of many genes and recruits histone transacetylase. Its mutations are related to many cancers.

The term "histone modification" used herein indicates a variety of modifications to histone, such as acetylation, methylation, demethylation, phosphorylation, adenylation, ubiquitination, and ADP ribosylation. In particular, the histone modification includes the demethylation of histone.

The term "object" used herein refers to mammals, such as human being. Other animals may also be included, for example domestic animals (e.g., dog and cat), poultry (such as cattle, sheep, swine, and horse), or laboratory animals (such as monkey, rat, mouse, rabbit, and guinea pig).

The term "consistency", "percent consistency", "homology", or "identity" used herein refers to the sequence identity between two amino acid sequences or nucleic acid sequences. The percent consistency may be determined by the alignment of two sequences, and it refers to the number of identical residues (i.e., amino acids or nucleotides) at positions common to the compared sequences. Sequence alignment and comparison may be carried out by the standard algorithms of the art (for example, Smith and Waterman, 1981, Adv. Appl. Math. 2:482; Needleman and Wunsch, 1970, J. Mol. Biol. 48:443; Pearson and Lipman, 1988, Proc. Natl. Acad. Sci., USA, 85:2444) or a computerized version of these algorithms (Wisconsin Genetics Software Package Release 7.0, Genetics Computer Group, 575 Science Drive, Madison, Wis.). The computerized version is publicly available as BLAST and FASTA. Additionally, the ENTREZ available from the National Institute of Health (Bethesda Md.) may be used for sequence comparison. When BLAST and gapped BLAST programs are used, the default parameters of the respective programs (such as BLASTN, which is available on the internet site of the National Center for Biotechnology Information) may be used. In one embodiment, GCG with a gap weight of 1 may be used to determine the percent identity between two sequences, such that each amino acid gap is given a weight as if it is a single amino acid mismatch between the two sequences. Alternatively, ALIGN program (version 2.0), which is a part of GCG (Accelrys, San Diego, Calif.) sequence alignment software package, may be used.

The term "vector" used herein is used in the meaning well known by those skilled in the art and may be an expression vector. The vector may include viruses (such as poxvirus, adenovirus, and baculovirus); yeast vectors, bacteriophages, chromosomes, artificial chromosomes, plasmids, cosmids, episome vectors, and mRNA vectors, or may be chemically synthesized directly. Preferably, the virus vector is a retrovirus and/or lentivirus vector. More preferably, the retrovirus is a pMXs vector.

The term "excessive" used herein indicates being significantly higher than the normal level, and particularly indicates that the expression of a polypeptide is statistically significantly higher that in normal cells. Preferably, it is higher by 20%, 50%, 100%, 200%, or even 5, 10, or 100 times.

The term "over-expression" used herein indicates that the expression level is significantly higher than the normal level, and particularly indicates that the expression of a polypeptide is statistically significantly higher that in normal cells. Preferably, it is higher by 20%, 50%, 100%, 200%, or even 5, 10, or 100 times.

The term "incorporation" used herein indicates a process to introduce exogenous substances (such as nucleic acids or proteins) into cells by, for example, calcium phosphate transfection, virus infection, liposome transfection, electroporation, gene gun or the like.

Herein, delivering an exogenous polypeptide into cells may be carried out by various methods, for example, by transporters or transport factors, and preferably, by liposome, bacterial polypeptide fragments or the like (refer to WO2002/079417, the content of which is incorporated herein by reference).

The cells that may be used in the method of the present invention are preferably mammalian cells, and more preferably human and mouse cells. In particular, the cells are somatic cells, such as epithelial cells, neural cells, fibroblasts, endothelial cells, myocytes, haematopoietic cells, immunocytes, and lymphocytes. More particularly, the cells are pancreatic beta cells, adult neural stem cells, hepatocytes, gastric cells, mature B cells, haematopoietic cells, meningocytes, adipose-derived stem cells, cord blood cells, peripheral blood CD34 positive cells, and keratinocytes.

Example 1

1. Construction of Vectors Comprising Jhdm1a and Jhdm1b Coding Regions a. Design of Primers for Cloning The sequence data of cDNAs of Jhdm1a and Jhdm1b were obtained from http://www.ncbi.nlm.nih.gov/pubmed, wherein the sequence of the cloning region of the Jhdm1a cDNA is SEQ ID NO: 1, and the sequence of the cloning region of the Jhdm1b cDNA is SEQ ID NO: 2. The coding sequences of Jhdm1a and Jhdm1b were amplified by designing specific primers.

The base sequence of Jhdm1a upstream primer is shown as SEQ ID NO: 3;

The base sequence of Jhdm1a downstream primer is shown as SEQ ID NO: 4;

The base sequence of Jhdm1b upstream primer is shown as SEQ ID NO: 5;

The base sequence of Jhdm1b downstream primer is shown as SEQ ID NO: 6;

b. Amplification of Coding Sequences by RT-PCR

Total mRNAs were extracted from isolated ICR mouse embryonic fibroblasts (MEFs) and human H1 embryonic stem cells according to the following method: a culture medium was removed from a culture tray, cells were rinsed with 3-5 ml of normal saline (PBS) (Gibco), and the rinsing solution is discarded. Then, 1 ml of cell lysate Trizol (Takara) was added into the culture tray, and a pipet was used to draw the resulting mixture solution and gently blow the cells so that they were completely dissolved in the lysate. Next, they were transferred into a clear 1.5 ml centrifuge tube to be stored at −80° C. or immediately subjected to the following extraction step. Afterwards, 200 μl of trichloromethane was added thereto, and the mixture were well mixed by turning the tube up and down for about 30 seconds and then centrifuged at 4° C. at 12000 rpm for 5 minutes. The supernatant was carefully drawn and transferred into a clear 1.5 ml centrifuge tube and then an equal volume of isopropanol was added thereto. They were well mixed, allowed to stand at the room temperature for 5 minutes, and then centrifuged at 4° C. at 12000 rpm for 5 minutes, at which time a small white precipitate was found at the bottom of the tube. The supernatant was discarded carefully, and next, 500 μl of an 80% ethanol solution was added into the tube to rinse away residual isopropanol. The tube was centrifuged at 12000 rpm to remove the ethanol solution. The centrifugate was kept at the room temperature for 30 minutes so that the white total mRNAs at the bottom of the tube were fully dried. Next, 30-50 μl of double distilled water was added into the centrifuge tube to incubate at 55° C. for 30 minutes. Afterward, the tube was taken out and measured for the concentration of total mRNAs by a spectrophotometer. The extracted total mRNAs were stored at −80° C. or directly used for preparing cDNAs by reverse transcription for later use.

The specific process and method of reverse transcription are as follows. Generally, 1 μg of total mRNAs were taken for reverse transcription, to which oligodT (Takara), dNTP (Takara), RTace (Toyobo), RT buffer and RRI (RNAse inhibitor, Takara), and RNase/DNase-free water were added. The mixture reacted on a PCR instrument at 42° C. for 60 minutes, was incubated at 98° C. for 5 minutes, and was then cooled down to the room temperature. After the reverse transcription succeeded, 0.5 μl of the reaction was taken out to act as the template to amplify the target gene by PCR using the primers designed by the above method. The reagents used include high-fidelity polymerase KOD and its buffer (Toyobo), dNTPs (Takara), and primers. The following process was run on the PCR instrument: denaturation at 96° C. for 5 minutes, at 95° C. for 30 seconds, annealing at 60° C. for 25 seconds, and elongation at 68° C. for 3.5 minutes; the 2-4 steps were repeated for 32 times.

c. Plasmid Construction

Figure 13:
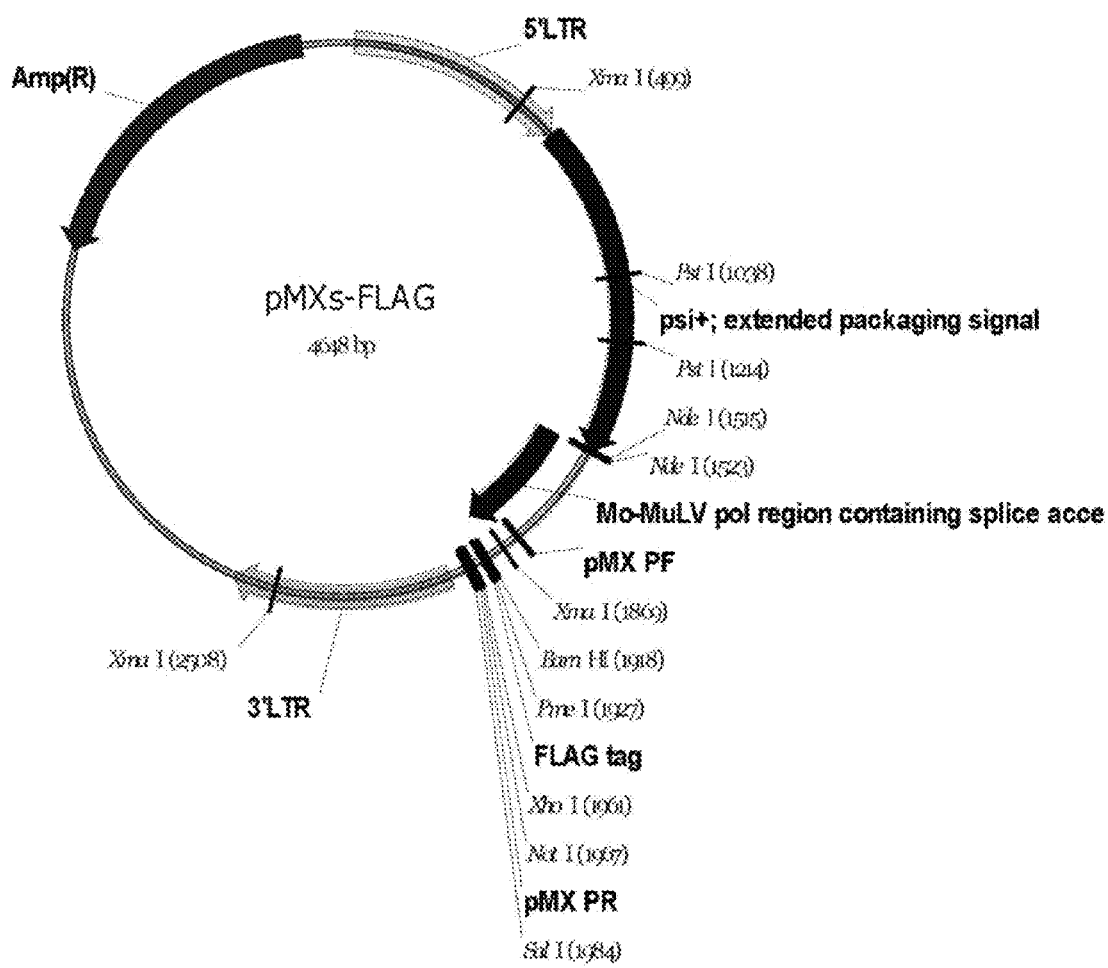
FIG. 13 shows the spectrum of the pMXs-FLAG plasmid.

Please refer to FIG. 13. After the amplification was completed, the PCR product was subjected to agarose gel electrophoresis and PCR fragments were extracted using a gel extraction kit (TIANGEN, DP214-03). The pMXs vector (purchased from addgene, and inserted with multiple cloning sites and FLAG labeling sequences) was used. The modified pMXs vector is called pMXs-FLAG, the plasmid presentation of which is shown in FIG. 13. The vector was cleaved with pmel and dephosphorylated with calf intestinal alkaline phosphatase (CTAP) so as to avoid its self-ligation. The treated vector was recovered using the gel extraction kit (TIANGEN, DP214-03) for later use. The pMX-FLAG vector and the gene fragments of Jhdm1a/Jhdm1b were ligated by a ligation kit (Takara, DNA Ligation Kit), and then the ligating product was used to transform competent *E. Coli*. The positive clones were selected, the plasmids were extracted and sequenced, and finally plasmids were prepared in a large scale.

2. Introducing the Coding Sequences of Jhdm1a/Jhdm1b and the Pluripotent Stem Cell Inducing Factor (Transcription Factor) into Mouse Embryonic Fibroblasts Unless specifically stated, the mouse based somatic cell reprogramming was carried out by the following manner in all cases.

Culture Medium

The culture medium for feeder layer cells, MEF cells, and PlatE cells consists of: high glucose basal medium DMEM (Gibco), plus 10% fetal bovine serum (FBS, PAA).

Inducing medium: the present invention used an inducing medium that is conventional in the laboratory, and the composition of a preferred inducing medium includes DMEM high glucose medium (Gibco), 15% fetal bovine serum (FBS, Gibco), 0.1 mM nonessential amino acid (NEAA, Gibco), 2 mML-glutamine (Glutamax, Gibco), 1 mM sodium pyruvate (Gibco), 55 μM β-mercaptoethanol (β-ME, Gibco), penicillin (50 U/mL) and streptomycin (50 μg/mL), leukemia inhibitory factor 1000 U/ml (LIF, Millipore), and as necessary, 50 μg/mL vitamin C (sigma).

Stem cell culture medium: the present invention used a stem cell culture medium that is conventional in the laboratory, and preferably the mES stem cell culture medium, the composition of which consists of: high glucose DMEM medium (Gibco) supplemented with 15% fetal bovine serum, 0.1 mM nonessential amino acid (NEAA, Gibco), 2 mM L-glutamine (Glutamax, Gibco), 1 mM sodium pyruvate (Gibco), 55 μM β-mercaptoethanol (Gibco), penicillin (50 U/mL) and streptomycin (50 μg/mL), and leukemia inhibitory factor 1000 U/ml (LIF, Millipore). 50 μg/mL vitamin C (sigma) are incorporated as necessary.

KSR serum-free culture medium: KSR, the abbreviation of Knockout Serum Replace, is a commercialized serum replacing stem cell culture additive and is used as a complete KSR serum-free medium for culturing stem cells or iPS clones, the composition of which consists of: KNOCKOUT DMED (a basal medium with optimized osmotic pressure that is suitable for culturing stem cells), a 15% KSR additive, 0.1 mM nonessential amino acid (NEAA, Gibco), 2 mM L-glutamine (Glutamax, Gibco), 1 mM sodium pyruvate (Gibco), 55 μM β-mercaptoethanol (β-ME, Gibco), penicillin (50 U/mL) and streptomycin (50 μg/mL), leukemia inhibitory factor 1000 U/ml (LIF, Millipore). All the iPS processes and cloning culture media are supplemented with mouse leukemia inhibitory factor (LIF, millipore, trade name: ESGRO, a growth factor that inhibits the differentiation of mouse stem cells) at a final concentration of 1000 U/ml.

3. Cells for Reprogramming

All the somatic cells for reprogramming are OG2 mouse embryonic fibroblasts (homemade), the passage number of which does not exceed three. One property of the OG2 mouse is that there is a green fluorescence protein (GFP) under the control of the Oct4 promoter that is specifically expressed by the stem cells. In reprogramming, when the endogenous Oct4 of the OG2 mouse embryonic fibroblasts is activated, the green fluorescence protein is expressed concomitantly. As observed through a fluorescence microscope, the successfully reprogrammed cells or cloned cell aggregates are green, and it is easy to compare the reprogramming efficiencies at different conditions by directly adding up the number of reprogrammed clones, i.e., the number of green fluorescence clones, or by analyzing the proportion of green fluorescence cells through a flow cytometer.

The reprogrammed cells were prepared as follows. The cells were seeded in 12-well plates (Corning) at a density of 20000 cells per well, and after 6-18 hours, were infected with viruses with the mouse reprogramming factor based on the density and the state of the cells.

4. Preparation of Viruses

The transcription factors for reprogramming include the retrovirus vector pMXs for cDNAs of mouse Oct4, Sox2, Klf4, and c-Myc (from Addgene, numbered Plasmid 13366, Plasmid 13367, Plasmid 13370, and Plasmid 13375 respectively); Oct4, NCBI accession number: NM_013663; Sox2, NCBI accession number: NM_011443; Klf4, NCBI accession number: 010637; and c-Myc, NCBI accession number: NM_001177353. The reprogramming factor plasmids on the pMX vector were transfected into the viral packaging cells (PlatE) by using a homemade calcium phosphate transfection reagent, and the specific process is: 7500000 PlatE cells were seeded in a 10-cm-diameter culture tray (Corning), and 12 hours later, the old culture medium was replaced by 7.5 ml of a culture medium free of penicillin/streptomycin, and then the cells were placed into an incubator. Next, the transfection mixture was prepared: 25 μg of the plasmids were taken and placed into a 15 ml centrifuge tube, and thereto 156.25 μl of a 2 M calcium chloride solution was added sequentially and an appropriate amount of water was additionally added so that the total volume thereof was 1.25 ml; they were well mixed, and 1.25 ml of an HBS solution was added thereto; the resulting mixture was mixed well immediately, allowed to stand-still for 2 minutes, and then added dropwise into a PlatE culture tray and well mixed. 9-12 hours after the transfection, the old culture medium was replaced by 10 ml of a fresh culture solution; 48 hours after the transfection, the culture solution was collected and filtered with a 0.45 μm filter membrane to be used as the viral solution for first infection; thereto a fresh culture solution was added 24 hours later, and the culture solution was re-collected in this way to be used as the viral solution for second infection.

5. Infecting MEF Cells with the Virus

The infection was carried out in two rounds, wherein the inducing factors used infected the cells simultaneously, each well of the 12-well plates was infected with 1 ml of the virus, the second round of infection was carried out 24 hours after the first round of infection, and the viral solution was replaced with the mES culture medium (as described above) 24 hours after the second round of infection. The day of solution replacement was recorded as day 0 (D0); at different time points after infection, in the original wells, the number of GFP fluorescence clones was counted or the proportion of GFP fluorescence cells was analyzed using a flow cytometer as required by the experiment.

6. Culturing the Infected Cells Until Formation of Stem Cell Clones

Embryonic stem cell-like monoclones with a swollen shape and clear edges were picked out using glass needles and directly transferred into culture plates (Corning) laid with feeder layer cells (the feeder layer cells are ICR mouse fibroblasts treated with mitamycin) in advance to culture with the KSR culture medium. At day 2 after infection, the culture system was replaced with a fresh inducing medium, and afterward, the inducing medium was replaced everyday until the experiment was completed.

Based on the above method for producing stem cell clones, the experiments were carried out using different combinations of pluripotent stem cell inducing factors.

The combinations of pluripotent stem cell inducing factors are described as follows:

The combination of Klf4, Sox2, c-Myc, and Oct4 is abbreviated as SKOM.

The combination of Klf4, Sox2, and Oct4 is abbreviated as SKO.

The combination of Klf4 and Oct4 is abbreviated as KO.

The combination of Sox2 and Oct4 is abbreviated as SO.

The combination of Oct4 and Jhdm1b is abbreviated as OB.

C4, C14, C15, and C16 are the four clones picked out from the OB induced reprogrammed cells.

Figure 2:
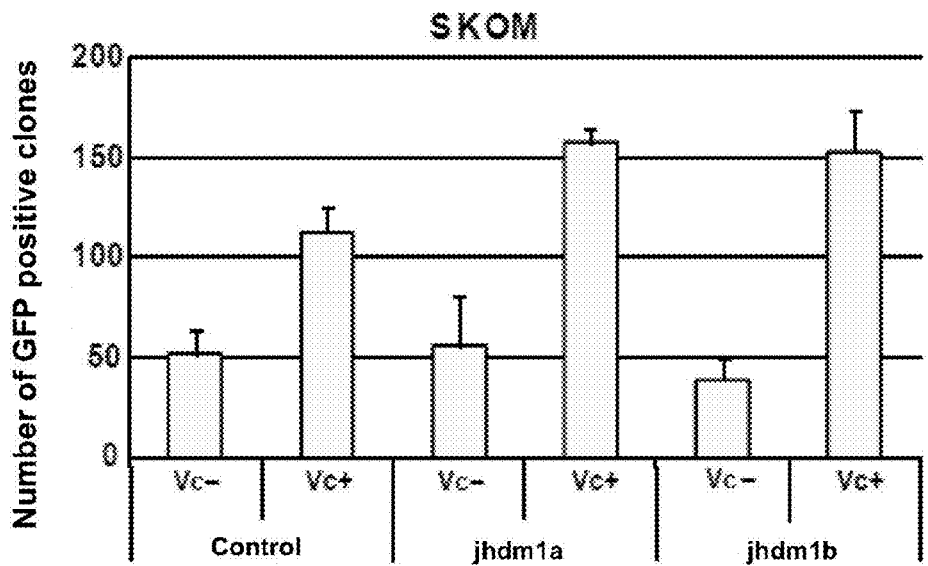
FIG. 2 shows data indicating that Jhdm1a or Jhdm1b promotes the efficiency of reprogramming mediated by SKOM.
Figure 3:
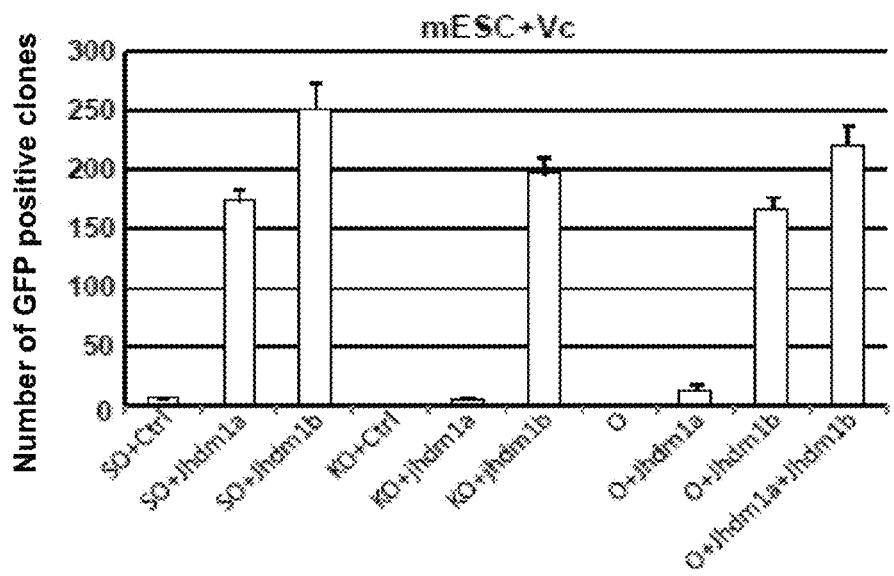
FIG. 3 shows that in the presence of vitamin C, Jhdm1a and Jhdm1b act together to enable re-programming only using SO, KO, and Oct4.

The results of the experiments using the combinations of stem cell inducing factors are as follows:

Referring to FIG. 1, no matter whether vitamin C was present or not, Jhdm1a or Jhdm1b obviously improved the efficiency of reprogramming, and in the presence of vitamin C, the improvement was more significant. FIG. 1 shows the data that Jhdm1a or Jhdm1b improved the efficiency of inducing pluripotent stem cells as mediated by SKO, wherein the control is a pMXs-FLAG empty vector with no gene sequence inserted therein;

Referring to FIG. 2, no matter whether vitamin C was present or not, Jhdm1a or Jhdm1b obviously improved the efficiency of reprogramming, and in the presence of vitamin C, the improvement was more significant. FIG. 2 shows the data that Jhdm1a or Jhdm1b improved the efficiency of inducing pluripotent stem cells as mediated by SKOM, wherein the control is a pMXs-FLAG empty vector with no gene sequence inserted therein;

Referring to FIG. 3, in the presence of vitamin C, Jhdm1a and Jhdm1b acted together to enable the induction of pluripotent stem cells only in the availability of SO, KO, or Oct4, wherein mESC+Vc indicates that the culture medium used in the induction is stem cell culture medium mES supplemented with 50 μg/ml vitamin C, and the control is a pMXs-FLAG empty vector.

Therefore, the present invention reaches a conclusion that Jhdm1a and Jhdm1b can significantly improve the efficiency of inducing pluripotent stem cells, greatly reduce the types of transcription factors required to be incorporated while maintaining a high reprogramming efficiency, which provides great benefits for reducing the accumulation of reprogrammed cell mutations and reducing their carcinogenecity. In addition, the method of the present invention also improves the operability of the reprogramming technique, reduces the operative difficulty, and facilitates subsequent medical applications.

Example 2

Identification of the Induced Pluripotent Stem Cells from the Example 1

As shown in FIG. 3 and FIG. 6 to FIG. 10, a series of identification experiments were carried out on pluripotent stem cell clones induced by Oct4 and Jhdm1b to verify whether they are iPS cells (induced pluripotent stem cells). The identification experiments include: quantitative PCR, immunofluorescence assay of their surface markers, promoter methylation degree analysis, karyotype identification, chimera formation, and so on.

Quantitative PCR Experiments:

All the quantitative PCR experiments were conducted in a CFX-96 type quantitative PCR instrument from Biorad using a kit from Takara, and the reaction conditions were 95° C., 2 minutes, 95° C., 10 seconds, 60° C., 30 seconds, reading the fluorescence value, repeating for 40 cycles.

Analysis of Methylation of the Promoter Region

The analysis was carried out by sodium bisulphite sequencing. The genomic DNAs in the target cells were extracted (Promega, Wizard® Genomic DNA Purification Kit), the concentration was measured, approximately 2 µg of DNAs were placed into a 1.5 ml EP tube where they were diluted with ddH20 to 50 µl, thereto 5.5 µl of freshly prepared 3 M NaOH was added, and the resulting solution was treated in a water bath at 42° C. for 30 minutes; next, the solution was taken out, 30 µl of 10 mM hydroquinone (sigma) was added into the mixture solution after the water bath treatment, and then 520 µl of 3.6 M sodium bisulphite (Sigma, S9000) was additionally added into the solution after the water bath treatment; the EP tube was wrapped with aluminum foil paper outside to avoid light, and the solution was well mixed by gently turning the EP tube up and down; 200 µl of paraffin oil was added thereto so as to prevent evaporation of water and oxidization, and the solution was treated in a water bath at 50° C. in darkness for 16 hours.

Next, the tip of a pipet was put below the paraffin oil layer to draw the mixture solution into a clear 1.5 ml centrifuge tube, and the modified DNAs were recovered using a Promega Wizard Cleanup DNA purification and retraction system (Promega, A7280), and then stored at −20° C. or subjected to a further experiment. 50 ng of the above extracted DNAs were taken as the template to conduct the PCR reaction. Afterward, the PCR product was recovered by gel extraction (TIANGEN, DP214-03), and the PCR product and a T vector (Takara) were then ligated and transformed. The positive clones were selected and sent to a sequencing company for sequencing, and the results were compared to statistically analyze the methylation of the CpG islands.

Identification of Karyotype of iPS Cells

The identification of karyotype of iPS cells was conducted according to the following method: 2-3 hours before harvesting, to the cells to be analyzed for karyotype, 0.1 ml of 5 µg/ml colchicine (commercially available, with a final concentration of 0.1 µg/ml) was added. They were well mixed, further cultured for 2-3 hours, transferred into a 10 ml centrifuge tube, and then centrifuged at 1500-2000 rpm for 10 minutes. The supernatant was discarded, and an 8 ml of a hypotonic solution (0.075 M KCl, preheated at 37° C.) was added to the tube. The cell precipitate was blown homogenously and placed in an incubator at 37° C. for half an hour. Thereto, 1 ml of a freshly prepared stationary liquid (a mixture of methanol and glacial acetic acid at a volume ratio of 3:1, commercially available) was added. The resulting mixture was gently mixed and centrifuged at the same rotation speed for the same period of time as the above. The supernatant was drawn off. 8 mL of the stationary liquid was added thereto. The cells were adequately mixed, fixed at the room temperature for at least half an hour, and centrifuged again. The supernatant was discarded, and a fresh stationary liquid was added thereto to further fix the cells for at least half an hour (desirably overnight). To the cell precipitate obtained after centrifugation and removal of the supernatant, about 0.2 ml of a fresh stationary liquid was added, and the resulting mixture was well mixed. The resulting cell suspension was dropped onto pre-cooled slides (it is advisable to drop 3 drops of the cell suspension on each slide) which were then baked on an alcohol lamp. The cells were then cooled down and banded.

Blastula Chimera Test

In the blastula chimera test, iPS cells were injected into the blastocoele of donor mice, and then the injected blastulas were transplanted into the uteruses of pseudopregnant female mice to make chimeric mice. Whether the born mice produce chimera was determined based on their coat color.

Figure 5:
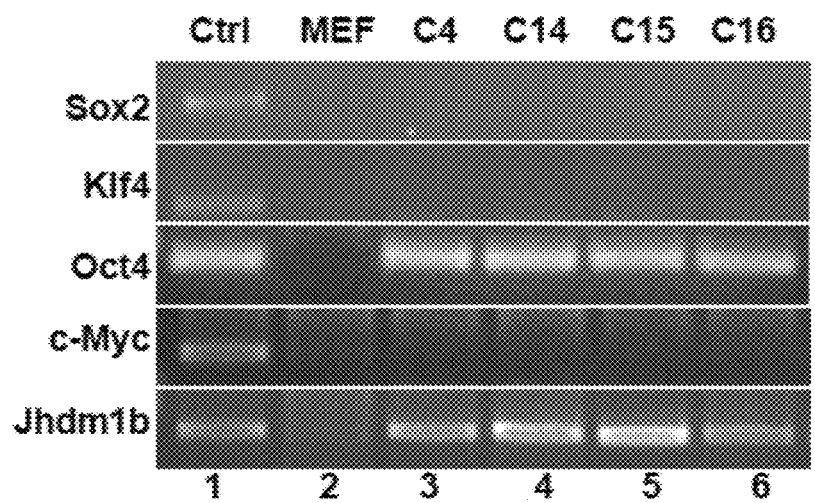
FIG. 5 shows the results of PCR amplification of the genomic DNAs of the pluripotent stem cell clones, indicating that in the genomes of the OB-induced pluripotent stem cell clones C4, C14, C15 and C16, only Oct4 and Jhdm1b are integrated, wherein the control is the genomic DNAs extracted from cells infected with Sox2, Klf4, Oct4, c-Myc and Jhdm1b, and MEF indicates genomic DNAs extracted from mouse embryonic fibroblasts.
Figure 6:
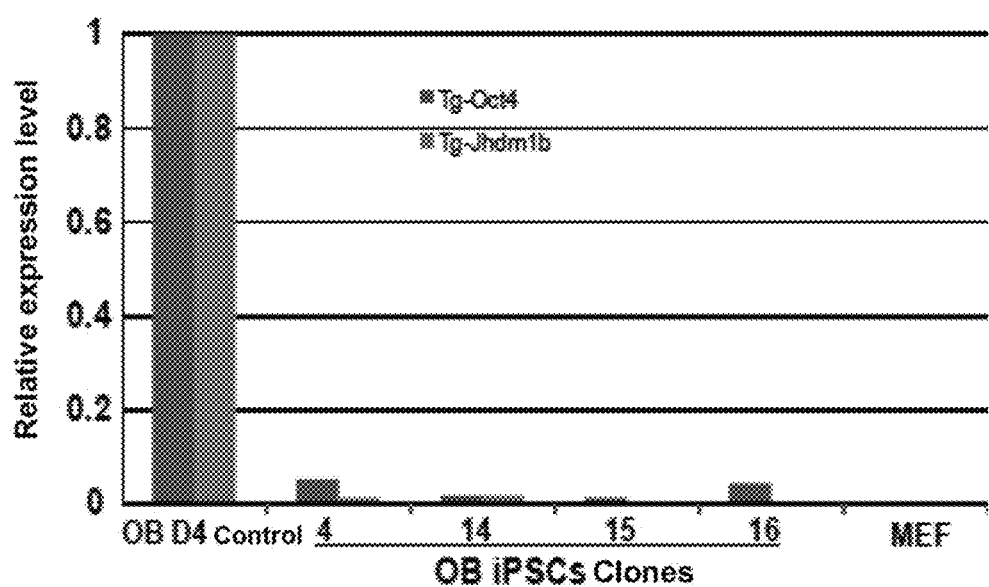
FIG. 6 shows the results of quantitative PCR, indicating that exogenous genes of the OB-induced pluripotent stem cell clones C4, C14, C15 and C16 are silently expressed, wherein the OB D4 control is a cDNA template obtained by reverse transcription of mRNAs extracted from the cells that have been infected with Oct4 and Jhdm1b and cultured for 4 days, and MEF is the mouse embryonic fibroblast.
Figure 7:
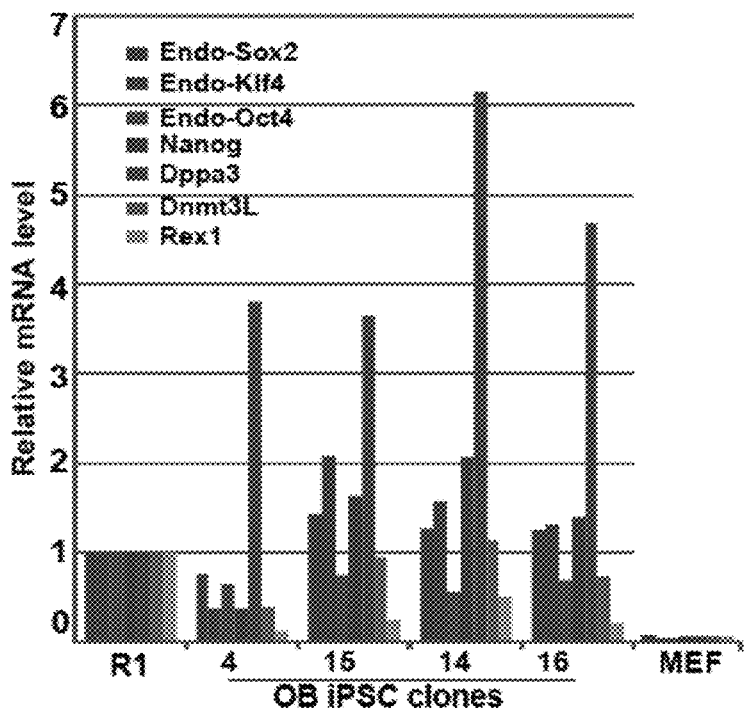
FIG. 7 shows the results of real-time quantitative PCR, indicating that the OB-induced pluripotent stem cell clones C4, C14, C15 and C16 express embryonic stem cell specific genes, wherein R1 is the mouse embryonic stem cell line, and MEF is the mouse embryonic fibroblast.

Experiments were carried out according to the above method, and the results are analyzed as follows:

Referring to FIG. 5, the PCR amplification results of the genomic DNAs of pluripotent stem cell clones show that, in the genomes of OB-induced pluripotent stem cell clones C4, C14, C15, and C16, only Oct4 is integrated with Jhdm1b, wherein the control is genomic DNAs extracted from cells infected with Sox2, klf4, oct4, cMyc, and Jhdm1b, and MEF indicates genomic DNAs extracted from mouse embryonic fibroblasts;

Referring to FIG. 6, the results of quantitative PCR show that exogenous genes of the OB-induced pluripotent stem cell clones C4, C14, C15, and C16 were silently expressed, wherein the OB D4 control is a cDNA template obtained by reverse transcription of mRNAs extracted from cells that have been infected with Oct4 and Jhdm1b and cultured for 4 days, and MEF is mouse embryonic fibroblast;

Refer to FIG. 7. As shown in FIG. 7, the results of real-time quantitative PCR show that the OB-induced pluripotent stem cell clones C4, C14, C15, and C16 expressed embryonic stem cell specific genes, wherein R1 is mouse embryonic stem cell line, and MEF is mouse embryonic fibroblast; the expression level of endogenous embryonic stem cell transcription factors in the stem cells obtained by using the combination of Oct4 with Jhdm1b was substantially consistent with that in the embryonic stem cells. This indicates that the OB-induced pluripotent stem cell clones C4, C14, C15, and C16 express embryonic stem cell specific genes, and thus indicates that the pluripotent stem cells induced by the method of the present invention have the characteristics of pluripotent stem cells.

Figure 8:
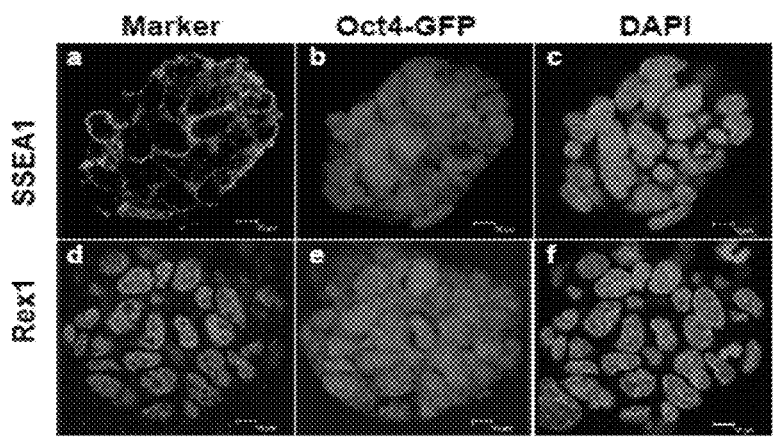
FIG. 8 shows the results of immunofluorescence, indicating that the OB-induced pluripotent stem cell clone C14 expresses embryonic stem cell specific gene Rex1 and embryonic stem cell specific surface marker SSEA-1, wherein Marker represents a stem cell specific marker molecule (i.e., Rex1 or SSEA-1)

Refer to FIG. 8. As shown in FIG. 8, the immunofluorescence results show that the pluripotent stem cells obtained through OB expressed SSEA-1 on the surface and expressed Rex1 as well.

Figure 9:
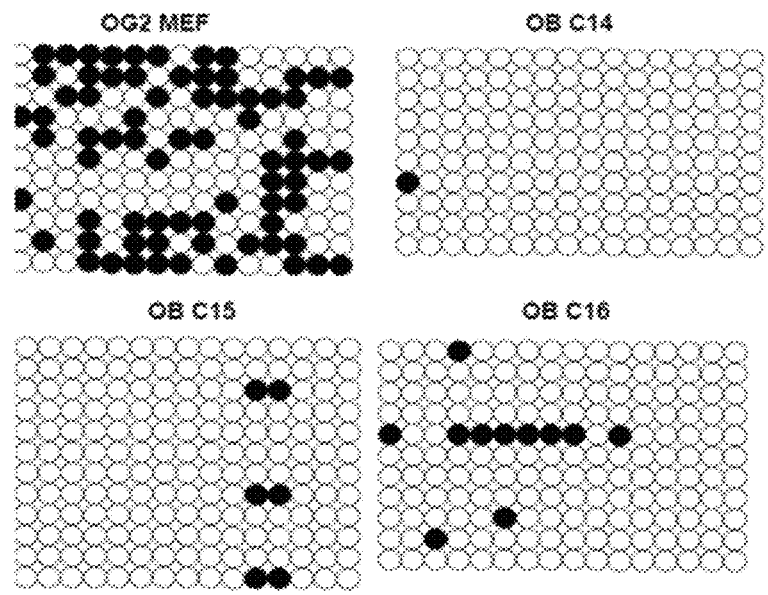
FIG. 9 shows the analysis results of measured methylation of CpGs in a region of Oct4 adjacent to the promoter in mouse embryonic fibroblasts and induced pluripotent stem cells.

Refer to FIG. 9 which shows the analysis of methylation of CpG islands in the Oct4 promoter region, wherein the CpG islands of the donor cells were methylated, while the CpG islands at the corresponding positions of the induced pluripotent stem cells were significantly demethylated.

Figure 10:
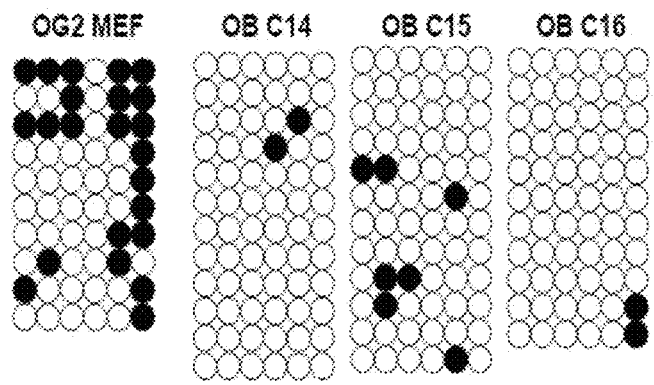
FIG. 10 shows the analysis results of measured methylation of CpGs in a region of Nanog adjacent to the promoter in mouse embryonic fibroblasts and induced pluripotent stem cells.

Refer to FIG. 10 which shows the analysis of methylation of CpG islands in the Nanog promoter region, wherein OB-C14, OB-C15, and OB-C16 are three pluripotent stem cells induced by Oct4 and Jhdm1b. The black parts indicate methylation, and the white parts indicate absence of methylation. The CpG islands of the donor cells were methylated, while the CpG islands at the corresponding positions of the induced pluripotent stem cells were significantly demethylated; Nanog and Oct4 are genes that are specifically expressed by embryonic stem cells and their expression states are closely related to the cell fate. These results show that the cells obtained by using the OB group had changed fate, that is to say, they were induced into pluripotent stem cells.

Figures 11, 12:
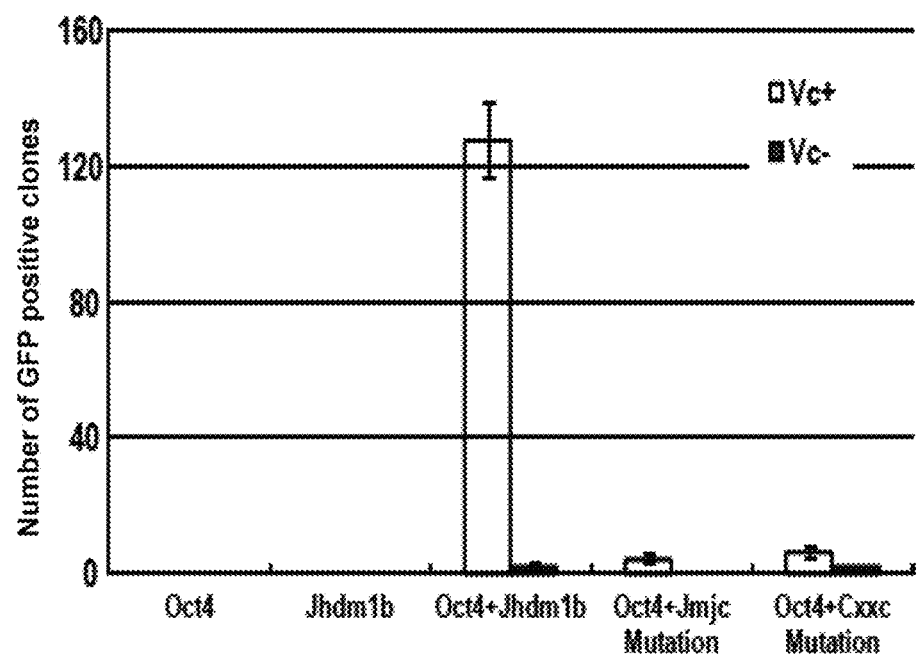
FIG. 11 shows the karyograms of Oct4 and Jhdm1b induced pluripotent stem cells.
FIG. 12 shows the efficiencies of inducing pluripotent stem cells by the various mutants of Jhdm1b. The Jmjc mutation involves mutating histidine at position 221, isoleucine at position 222, and aspartic acid at position 223 into alanine; the CxxC mutation involves mutating cysteine at positions 586, 589, and 592 into alanine.

Refer to FIG. 11 which shows that the stem cells obtained by the method of the present invention had normal karyotypes, wherein OB-14, OB-C15, and OB-C16 are three pluripotent stem cells induced by Oct4 and Jhdm1b and have normal karyotypes.

Figure 4:
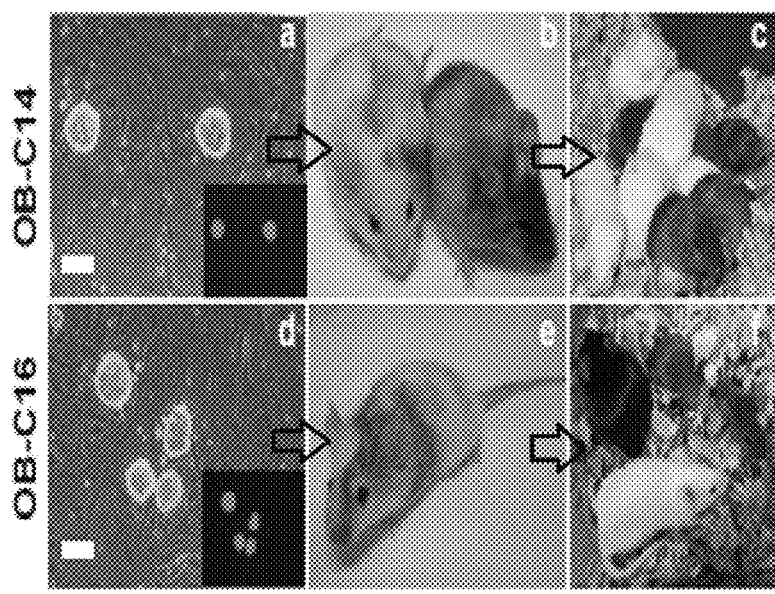
In FIG. 4, a and d are microphotographs of the induced pluripotent stem cells that are finally formed by using Oct4+Jhdm1b (briefed as OB); b and e are photographs of chimeric offspring that are developed after the induced pluripotent stem cells finally formed by using OB are injected into the blastula; and c and f are photographs of the offspring that are generated after the chimeras mated with wild type mice, wherein the chimeras are developed after the induced pluripotent stem cells finally formed by using OB are injected into the blastula)

Refer to FIG. 4. As shown in FIG. 4, a and d are the microphotographs of the induced pluripotent stem cells finally formed by Oct4+Jhdm1b (abbreviated as OB); b and e are the photographs of chimeric offspring that are developed after the induced pluripotent stem cells finally formed by OB are injected into the blastula; c and f are photographs of the offspring that are generated after the chimeras mated with wild type mice, wherein the chimeras are developed after the induced pluripotent stem cells finally formed by using OB are injected into the blastula. This shows that the stem cells obtained by the method of the present invention can form chimera, wherein the donor cells are induced pluripotent stem cells originated from OG2/129 cells, while the pseudopregnant mice are ICR mice fed in the laboratory. The chimeras were capable of transmitting the original donor cells to the offspring through the germ line, indicating that such stem cells have good quality.

Determination of the Functionalities of Jhdm1b Variants:

Refer to FIG. 12. As shown in FIG. 12, the Jhdm1b variants that are mutated did not have the activity of improving the reprogramming efficiency, so the DNA binding domain (CXXC) and the catalytic domain (Jmic) of Jhdm1b are necessary for reprogramming and a lack of either of them will fail to promote the process of reprogramming. Furthermore, the combination of Oct4 with Jhdm1b can complete reprogramming in a common culture medium, and achieves more significant effects in the presence of vitamin C.

What are described above are the embodiments of the present invention and are not to limit the patent scope of the present invention thereto. All equivalent structures or equivalent process changes made by utilizing the description and the appended drawings of the present invention, or the direct or indirect applications thereof in other relevant technical fields, are within the patent scope of the present invention in the similar way.

What is claimed is:

1. A method for generating induced pluripotent stem cell clones, the method comprising the steps of:
   a. introducing a retroviral expression vector consisting of (i) Oct4 and Jhdm1b or (ii) Oct4, Klf4 and Jhdm1b into mouse embryonic fibroblast; and
   b. culturing the fibroblasts in an inducing medium comprising vitamin C to induce pluripotent stem cell clones.

2. The method of claim 1, wherein the retroviral expression vector is a pMXs vector.

3. A method for generating induced pluripotent stem cell clones, the method comprising the steps of:
   a. introducing a retroviral expression vector consisting of (i) Oct4, Jhdm1a and Jhdm1b or (ii) Oct4, Klf4, Jhdm1a and Jhdm1b into mouse embryonic fibroblasts; and
   b. culturing the fibroblasts in an inducing medium comprising vitamin C to induce pluripotent stem cell clones.

4. The method of claim 1, further comprising a step c: culturing and expanding the induced pluripotent stem cell clones in a stem cell culture medium in the presence of feeder cells.

5. The method of claim 3, further comprising a step c: culturing and expanding the induced pluripotent stem cell clones in a stem cell culture medium in the presence of feeder cells.

6. The method of claim 3, wherein the retroviral expression vector is a pMXs vector.

7. The method of claim 1, wherein the inducing medium includes DMEM high glucose medium, 15% fetal bovine serum, 0.1 mM nonessential amino acid, 2 mM L-glutamine, 1 mM sodium pyruvate, 55 µM β-mercaptoethanol, 50 U/mL penicillin, 50 µg/mL streptomycin, 1000 U/ml leukemia inhibitory factor, and 50 µg/mL vitamin C.

8. The method of claim 3, wherein the inducing medium includes DMEM high glucose medium, 15% fetal bovine serum, 0.1 mM nonessential amino acid, 2 mM L-glutamine, 1 mM sodium pyruvate, 55 µM β-mercaptoethanol, 50 U/mL penicillin, 50 µg/mL streptomycin, 1000 U/ml leukemia inhibitory factor, and 50 µg/mL vitamin C.

* * * * *

SEQUENCE LISTING

<160> NUMBER OF SEQ ID NOS: 8

<210> SEQ ID NO 1
<211> LENGTH: 3486
<212> TYPE: DNA
<213> ORGANISM: Artificial sequence
<220> FEATURE:
<223> OTHER INFORMATION: nucleotide acid sequence of coding regions for kdm2a

<400> SEQUENCE: 1

```
atggaacctg aagaagaaag gattcggtac agccagagat tgcgtggtac catgcgtcgt      60
cgctatgaag atgatggcat ttcagatgat gaaattgaag ggaaaagaac ttttgacttg     120
gaagagaagc tccaaaccaa caaatataat gccaattttg ttacttttat ggagggaaaa     180
gattttaatg tagagtatat ccagcggggt ggcttgagag acctctcat tttcaagaat      240 tctgatggac ttggaataaa gatgccggat ccagacttca cagtgaatga tgtcaaaatg     300
tgtgtgggga gtcgtcggat ggtggatgtc atggatgtga acacacagaa ggggattgaa     360
atgaccatgg cacaatggac acgatactat gagactccag aggaagagcg agaaaaactc     420
tataatgtta tcagcctaga gtttagccac accaggcttg agaatatggt gcagcggcct     480
tccacggtgg atttcattga ctgggtagat aacatgtggc caaggcactt gaaagaaagt     540
cagacagaat caacaaatgc catcttagag atgcagtacc ctaaagtgca aaagtactgt     600
ctaatgagtg ttcgaggctg ctatactgac ttccatgtgg attttggagg tacttctgtt     660
tggtatcaca tccaccaagg tggaaaggtc ttctggctca tccccctac agcccacaac       720 ctggagctgt acgagaattg gctgctatca gggaaacagg gagacatctt tctgggtgac     780
cgggtgtcag attgccaacg aattgagctc aagcagggct ataccttcgt tattccctca     840
ggttggattc atgctgtgta tactcctaca gacacattag tgtttggagg caattttttg     900
catagcttca acatccccat gcaattaaag atatacagca ttgaagatcg aacacgggtt     960
ccaaataaat tccgttaccc attttactat gaaatgtgtt ggtatgtgtt ggagcgctat    1020
gtatactgca taaccaaccg atcccaccta actaaggatt tcagaaaga atcccttagc    1080 atggatatgg agttaaatga gttggagtct ggaaatggtg atgaggaagg ggtggacaga    1140
```

-continued

```
gaagcccgac gcatgaacaa taagcgatct gtgcttacca gccctgttgc taatggagtg      1200
aacctggatt acgatggact tggcaaagcc tgccgaagtc ttccaagtct gaagaaaact      1260
ttgtctggag actcatcctc agactctacc cggggatccc acaatggcca gtttgggat       1320 ccccaatgta gccctaaaaa ggataggcaa gtgcatctca cccattttga acttgaaggt      1380
cttcgatgtc ttgtagataa gttagagtca ctgccactgc acaagaagtg tgtccccaca      1440
ggaatagaag acgaagatgc tctgattgct gatgtaaaga ttttgctgga gaacttgcc       1500 agtagcgatc ccaagttagc cctcactgga gtccctatag tacagtggcc aaaaagggat      1560
aagcttaaat tccctaccag gccaaaggtg agggttccta caattcccat cacaaagcct      1620
cacaccatga agccagctcc acgcttaaca cctgtaaggc ctgctgcagc ctccccatt       1680 gtgtcaggag ccaggcggag aagagtgcgg tgcaggaaat gcaaagcttg tgtgcaagga      1740
gaatgtggag tctgccacta ctgcagggac atgaagaaat ttggtggacc tggacgcatg      1800
aagcaatcct gtgtcctccg acagtgctta gcacccagac tgcctcattc agttacgtgt      1860
tctctctgtg gagaagtaga tcagaatgaa gagacccagg actttgaaaa gaaactcatg      1920
gaatgctgca tctgcaacga gatagttcat cctggctgcc tccagatgga tggagggg       1980 ttgctgaacg aggaattgcc aaattgctgg gagtgtccaa agtgttacca ggaagacagc      2040
tcggacaaag cccagaagcg gaaaatagaa gagagtgatg aagaagctgt acaagccaaa      2100
gtcttacggc ccctgaggag ctgcgaggag cctctcacac ccccgcctca ctcacctact      2160
tccatgctgc agctcatcca cgacccggtt tctccccggg gtatggtgac tcggtcatcc      2220 cctgggctg gccccagcga ccaccacagt gccagccgtg atgaacgctt caaacggcgg      2280
cagttgctgc ggctacaagc caccgagcgc accatggtac gggaaaagga gaacaatccc      2340
agcggcaaaa aggagctgtc tgaagttgag aaagccaaga tccggggatc gtacctcact      2400
gtcactctac agaggcccac caaagagctc cacgggacat ccattgtgcc caagctgcag      2460
gccatcacgc cctcctctgc caaccttcgc cctaaccccc gcgtgctaat gcagcactgc      2520
ccagcccgaa acccccagca tggggatgag gaggggcttg gggagagga ggaggaagag       2580 gaggaggagg aggaagatga cagtgcagag gagggggtg cagccaggct gaatggccgg       2640
ggcagttggg ctcaggatgg agacgaaagc tggatgcagc gggaggtctg gatgtctgtc      2700
ttccgctacc tcagccgcaa agaactttgt gaatgtatgc gagtgtgcaa gacatggtat      2760
aaatggtgct gtgataaacg actttggaca aaaattgact tgagtaggtg taaggccatc      2820
gtaccacaag ctctcagtgg tatcatcaag cggcagccag taagcctcga cctcagctgg      2880
actaacatct ccaaaaagca gctgacatgg ctggtcaata ggctgccagg attaaaagac      2940
ctcctcctag caggctgttc ctggtctgca gtatctgccc tcagcacttc cagctgcccg      3000
cttctcagga cccttgatct tcggtgggca gtaggaatta agaccctca aattcgggac       3060 ttgctgactc cacccacaga taagccaggt caagacaatc gaagcaaact ccggaacatg      3120
actgacttcc ggctggcagg ccttgacatc acagatgcta ctctccgact catcattcgc      3180
cacatgcccc ttttgtctcg acttgacctc agtcactgca gtcaccttac agatcagtcc      3240
tccaacctac taactgctgt cgggtcttcc actcgatact cccttacaga gctcaatatg      3300
gcaggttgca ataaattgac agaccagacc ctgttcttcc taaggcgaat tgctaatgtc      3360
accttgattg accttcgagg atgcaaacag atcacgagaa aagcctgtga gcacttcatc      3420
tcagacttgt ccatcaacag cctctactgc ctgtctgatg agaaactgat acagaagatt      3480
agctaa                                                                  3486
```

<210> SEQ ID NO 2
<211> LENGTH: 3930
<212> TYPE: DNA
<213> ORGANISM: Artificial sequence
<220> FEATURE:
<223> OTHER INFORMATION: nucleotide acid sequence of coding regions for kdm2b

<400> SEQUENCE: 2

| | | | | | |
|---|---|---|---|---|---|
| atggaggcag | agaaagactc | tggaagaaga | ttgcgtgcga | ttgaccgcca | gagatacgac | 60 |
| gagaacgaag | acttgtcgga | cgtggaggaa | attgtcagcg | tccgtggctt | cagcctggag | 120 |
| gagaagctac | gtagccagtt | ataccagggg | gacttcgtgc | atgctatgga | aggcaaagat | 180 |
| tttaactatg | agtacgtaca | gagagaagct | ctcagggtcc | ccctggtttt | tcgggacaag | 240 |
| gatggactag | ggatcaagat | gccagaccct | gatttcacag | tccgagacgt | caaactcctg | 300 |
| gtggggagcc | gccgtttggt | ggatgtcatg | gacgtcaaca | cccagaaggg | taccgagatg | 360 |
| agcatgtccc | agtttgtgcg | ctactacgag | acaccagagg | cacagcggga | taaactgtac | 420 |
| aacgtcatca | gcctcgagtt | cagccatacg | aagctggagc | atctggtcaa | gcgtcccact | 480 |
| gtggtggacc | tggtcgactg | ggtggacaac | atgtggcctc | agcatctaaa | ggaaaagcag | 540 |
| acagaagcca | ccaatgccct | tgcagagatg | aagtacccca | agtgaaaaaa | gtactgtctg | 600 |
| atgagcgtga | agggctgttt | cactgacttc | acattgact | ttggaggcac | ctccgtgtgg | 660 |
| taccatgtgt | tccgtggtgg | caagatcttt | tggctgatcc | ctccaaccct | gcacaacttg | 720 |
| gctttgtacg | aggagtgggt | gctgtctggc | aaacagagcg | acatctttct | gggagaccgc | 780 |
| gtggaacgct | gccaaagaat | tgagctgaag | caaggctaca | cctttttcat | cccttccggt | 840 |
| tggatccatg | cggtttatac | gcctgtggac | tctctggtgt | tcggcgggaa | catcctgcat | 900 |
| agcttcaacg | tgcccatgca | gctgcggatc | tacgagatcg | aggacaggac | ccgggttcag | 960 |
| cccaagttcc | gttacccctt | ctactatgag | atgtgctggt | atgtcttgga | gagatatgtg | 1020 |
| tactgtgtga | cccagcgctc | ctacctcact | caggaatacc | agagagaatt | aatgcttatt | 1080 |
| gatgccccaa | gaaaaaccag | tgtagacggc | ttttcatccg | actcctggct | ggacatggag | 1140 |
| gaggagtcct | gcgagcagca | gccacaggag | gaagaggagg | aggaggagga | caaggaggag | 1200 |
| gaaggagatg | gtgcagataa | aacacccaag | ccacccaccg | atgaccccac | ctcacccacc | 1260 |
| agcaccccgc | ccgaagacca | ggacagcaca | gggaagaagc | ctaaagcccc | tgccatacgg | 1320 |
| ttcctcaaga | ggacgttgtc | caatgagtca | gaggaaagtg | tcaagtcgac | ctcgatgccc | 1380 |
| acggacgatc | ccaagacgcc | cacgggctcc | ccggccaccg | aggtttctac | caagtggact | 1440 |
| caccttaccg | aatttgaact | gaagggcttg | aaagccctgg | ttgaaaagct | agagtccctt | 1500 |
| ccggagaata | agaagtgtgt | ccctgaggga | atcgaggacc | ccaggcccct | cctggaaggt | 1560 |
| gtaaagaatg | tactgaaaga | gcacgtggat | gacgacccca | ccctggccat | caccggggtc | 1620 |
| cctgtggtca | gctggccaaa | gaaaactgca | agaaccgggt | ggtgggtcg | gcctaagggc | 1680 |
| aagttgggcc | cggcctcagc | ggtgaagttg | gctgccaacc | gaacaacagc | aggagctcgc | 1740 |
| aggcgccgga | cgcgatgccg | caagtgcgag | gcctgcctgc | ggacggagtg | tggagagtgc | 1800 |
| cacttttgca | aggacatgaa | gaagtttgga | ggtcctgggc | gcatgaagca | gagctgcatc | 1860 |
| atgcggcagt | gcatcgcgcc | agtgctgccc | cacaccgccg | tgtgccttgt | gtgtggcgag | 1920 |
| gcagggaagg | aggacacagt | ggaagaggaa | gaaggcaagt | taaccctcat | gctcatggaa | 1980 |
| tgctccatct | gcaacgagat | catccacccc | tggatgccta | agattaagga | atcggagggt | 2040 |

```
gtggtcaacg atgagcttcc caactgctgg gagtgtccga agtgtaacca tgccggcaag    2100
accgggaaac aaaagcgtgg ccctggcttt aagtatgcct ccaacctgcc tggctccttg    2160
ctcaaggagc agaagatgaa ccgggacaac aaggaagggc aagagcctgc caagcggaga    2220
agtgagtgtg aagaggctcc ccgtcgagg tcagacgagc accccaaaaa ggtgcctgca    2280
gatggcatcc tccgccgaaa gtctgatgat gtgcacctga ggaggaagcg aaatacgag    2340 aagcccaag agctgagtgg acgcaagcga gcctcgtcgc ttcaaacgtc ccccggttcc    2400
tcctctcacc tctcgccgag gcccctcta ggcagcagtc tcagcccttg gtggagatcc    2460
agtctcactt acttccagca gcagctaaaa cctggcaaag aagataagct tttcaggaaa    2520
aagcggcggt cctggaagaa cgctgaggat cgtctgtcac tggccaacaa gcccctcgg    2580 cgctttaagc aggaaccgga ggacgatctg cctgaggcac tcctaagac ccgggagagt    2640 gatcagtcac gttccagctc acccactgct ggtcccagca ctgagggagc tgaaggccca    2700
gaagagaaga aaaggtgaa gatgcgccgg aagcggcgac ttgttaacaa ggagctgagc    2760
aaagagctaa gcaaggagct caaccatgag atccaaaaga cggagagcac cctggctcac    2820
gagagccagc agcccatcaa gtcagagcct gagagcgaga cgacgagcc caagaggccc    2880 ttaagccact gcgagcgccc ccaccgcttc agcaaagggc tcaacggcac acctcgggag    2940
ctgcggcact cgctgggacc tggcctgcgt agtccacctc gtgttatgtc ccggcccccg    3000
ccctctgcat ccccaccaa gtgcatccag atggagcgtc acgtgatccg gccaccgccc    3060
atcagccccc cacctgactc gctgcccctg gatgatggag cagcccacgt catgcatagg    3120
gaggtgtgga tggcagtctt cagctacctc agccaccgag acctgtgtgt ctgcatgcgg    3180
gtctgcagga cctggaaccg ctggtgctgc gataagcggt tgtggacccg catcgacctg    3240
aaccgctgca agtccatcac accctgatg ctgagcggta tcatccggcg acagcctgtc    3300
tcccttgacc tcagttggac caacatctcc aagaagcagc tgagttggct catcaaccgg    3360
ttgcctgggc tccgagactt ggtgctgtca ggctgctcat ggatcgctgt ctcagccctc    3420
tgtagctcca gttgtccatt gctccggacc ctggatgtcc agtgggtaga aggactaaag    3480
gatgcccaga tgagggatct cctgtctcca cccacagaca caggccagg tcagatggac    3540 aatcggagca agctccggaa cattgtagag ctgcgcctag ctggcctgga catcacagat    3600
gtctccctgc ggctcattat tcgccatatg ccctgctct cgaagctcca actcagttac    3660
tgtaaccaca tcaatgacca gtccatcaac ctgctcactg ccgtcggcac caccccga    3720 gactcgctga cagaggtcaa cctatcgac tgtaataagg taactgacct gtgcctgtcc    3780
ttcttcaaac gctgtggaaa tatctgtcat attgacctga ggtactgcaa gcaagtcacc    3840
aaggaaggct gtgagcaatt catagctgaa atgtctgtga gtgtccaatt tgggcaagtg    3900
gaagagaaac tcctgcaaaa actaagttag                                    3930
```

<210> SEQ ID NO 3
<211> LENGTH: 21
<212> TYPE: DNA
<213> ORGANISM: Artificial sequence
<220> FEATURE:
<223> OTHER INFORMATION: KDM2B forward cloning primer sequence

<400> SEQUENCE: 3
atggaggcag agaaagactc t                                              21

<210> SEQ ID NO 4

-continued

```
<211> LENGTH: 23
<212> TYPE: DNA
<213> ORGANISM: Artificial sequence
<220> FEATURE:
<223> OTHER INFORMATION: KDM2B reverse cloning primer sequence

<400> SEQUENCE: 4
acttagtttt tgcaggagtt tct                                              23

<210> SEQ ID NO 5
<211> LENGTH: 25
<212> TYPE: DNA
<213> ORGANISM: Artificial sequence
<220> FEATURE:
<223> OTHER INFORMATION: KDM2A forward cloning primer sequence

<400> SEQUENCE: 5
atggaacctg aagaagaaag gattc                                            25

<210> SEQ ID NO 6
<211> LENGTH: 25
<212> TYPE: DNA
<213> ORGANISM: Artificial sequence
<220> FEATURE:
<223> OTHER INFORMATION: KDM2A reverse cloning primer sequence

<400> SEQUENCE: 6
ttagctaatc ttctgtatca gtttc                                            25

<210> SEQ ID NO 7
<211> LENGTH: 1162
<212> TYPE: PRT
<213> ORGANISM: Homo sapiens

<400> SEQUENCE: 7

Met Glu Pro Glu Glu Glu Arg Ile Arg Tyr Ser Gln Arg Leu Arg Gly
1               5                   10                  15

Thr Met Arg Arg Arg Tyr Glu Asp Asp Gly Ile Ser Asp Asp Glu Ile
            20                  25                  30

Glu Gly Lys Arg Thr Phe Asp Leu Glu Glu Lys Leu His Thr Asn Lys
        35                  40                  45

Tyr Asn Ala Asn Phe Val Thr Phe Met Glu Gly Lys Asp Phe Asn Val
    50                  55                  60

Glu Tyr Ile Gln Arg Gly Gly Leu Arg Asp Pro Leu Ile Phe Lys Asn
65                  70                  75                  80

Ser Asp Gly Leu Gly Ile Lys Met Pro Asp Pro Asp Phe Thr Val Asn
                85                  90                  95

Asp Val Lys Met Cys Val Gly Ser Arg Arg Met Val Asp Val Met Asp
            100                 105                 110

Val Asn Thr Gln Lys Gly Ile Glu Met Thr Met Ala Gln Trp Thr Arg
        115                 120                 125

Tyr Tyr Glu Thr Pro Glu Glu Arg Glu Lys Leu Tyr Asn Val Ile
    130                 135                 140

Ser Leu Glu Phe Ser His Thr Arg Leu Glu Asn Met Val Gln Arg Pro
145                 150                 155                 160

Ser Thr Val Asp Phe Ile Asp Trp Val Asp Asn Met Trp Pro Arg His
                165                 170                 175

Leu Lys Glu Ser Gln Thr Glu Ser Thr Asn Ala Ile Leu Glu Met Gln
            180                 185                 190

Tyr Pro Lys Val Gln Lys Tyr Cys Leu Met Ser Val Arg Gly Cys Tyr
```

```
            195                 200                 205
Thr Asp Phe His Val Asp Phe Gly Gly Thr Ser Val Trp Tyr His Ile
210                 215                 220

His Gln Gly Gly Lys Val Phe Trp Leu Ile Pro Pro Thr Ala His Asn
225                 230                 235                 240

Leu Glu Leu Tyr Glu Asn Trp Leu Leu Ser Gly Lys Gln Gly Asp Ile
                245                 250                 255

Phe Leu Gly Asp Arg Val Ser Asp Cys Gln Arg Ile Glu Leu Lys Gln
                260                 265                 270

Gly Tyr Thr Phe Val Ile Pro Ser Gly Trp Ile His Ala Val Tyr Thr
            275                 280                 285

Pro Thr Asp Thr Leu Val Phe Gly Gly Asn Phe Leu His Ser Phe Asn
290                 295                 300

Ile Pro Met Gln Leu Lys Ile Tyr Asn Ile Glu Asp Arg Thr Arg Val
305                 310                 315                 320

Pro Asn Lys Phe Arg Tyr Pro Phe Tyr Tyr Glu Met Cys Trp Tyr Val
                325                 330                 335

Leu Glu Arg Tyr Val Tyr Cys Ile Thr Asn Arg Ser His Leu Thr Lys
                340                 345                 350

Glu Phe Gln Lys Glu Ser Leu Ser Met Asp Leu Glu Leu Asn Gly Leu
            355                 360                 365

Glu Ser Gly Asn Gly Asp Glu Glu Ala Val Asp Arg Glu Pro Arg Arg
370                 375                 380

Leu Ser Ser Arg Arg Ser Val Leu Thr Ser Pro Val Ala Asn Gly Val
385                 390                 395                 400

Asn Leu Asp Tyr Asp Gly Leu Gly Lys Thr Cys Arg Ser Leu Pro Ser
                405                 410                 415

Leu Lys Lys Thr Leu Ala Gly Asp Ser Ser Asp Cys Ser Arg Gly
                420                 425                 430

Ser His Asn Gly Gln Val Trp Asp Pro Gln Cys Ala Pro Arg Lys Asp
            435                 440                 445

Arg Gln Val His Leu Thr His Phe Glu Leu Glu Gly Leu Arg Cys Leu
    450                 455                 460

Val Asp Lys Leu Glu Ser Leu Pro Leu His Lys Lys Cys Val Pro Thr
465                 470                 475                 480

Gly Ile Glu Asp Glu Asp Ala Leu Ile Ala Asp Val Lys Ile Leu Leu
                485                 490                 495

Glu Glu Leu Ala Asn Ser Asp Pro Lys Leu Ala Leu Thr Gly Val Pro
            500                 505                 510

Ile Val Gln Trp Pro Lys Arg Asp Lys Leu Lys Phe Pro Thr Arg Pro
            515                 520                 525

Lys Val Arg Val Pro Thr Ile Pro Ile Thr Lys Pro His Thr Met Lys
            530                 535                 540

Pro Ala Pro Arg Leu Thr Pro Val Arg Pro Ala Ala Ser Pro Ile
545                 550                 555                 560

Val Ser Gly Ala Arg Arg Arg Val Arg Cys Arg Lys Cys Lys Ala
                565                 570                 575

Cys Val Gln Gly Glu Cys Gly Val Cys His Tyr Cys Arg Asp Met Lys
            580                 585                 590

Lys Phe Gly Gly Pro Gly Arg Met Lys Gln Ser Cys Val Leu Arg Gln
            595                 600                 605

Cys Leu Ala Pro Arg Leu Pro His Ser Val Thr Cys Ser Leu Cys Gly
610                 615                 620
```

```
Glu Val Asp Gln Asn Glu Thr Gln Asp Phe Glu Lys Lys Leu Met
625                 630                 635                 640

Glu Cys Cys Ile Cys Asn Glu Ile Val His Pro Gly Cys Leu Gln Met
            645                 650                 655

Asp Gly Glu Gly Leu Leu Asn Glu Glu Leu Pro Asn Cys Trp Glu Cys
                660                 665                 670

Pro Lys Cys Tyr Gln Glu Asp Ser Ser Glu Lys Ala Gln Lys Arg Lys
            675                 680                 685

Met Glu Glu Ser Asp Glu Glu Ala Val Gln Ala Lys Val Leu Arg Pro
    690                 695                 700

Leu Arg Ser Cys Asp Glu Pro Leu Thr Pro Pro His Ser Pro Thr
705                 710                 715                 720

Ser Met Leu Gln Leu Ile His Asp Pro Val Ser Pro Arg Gly Met Val
                725                 730                 735

Thr Arg Ser Ser Pro Gly Ala Gly Pro Ser Asp His His Ser Ala Ser
            740                 745                 750

Arg Asp Glu Arg Phe Lys Arg Gln Leu Leu Arg Leu Gln Ala Thr
                755                 760                 765

Glu Arg Thr Met Val Arg Glu Lys Glu Asn Asn Pro Ser Gly Lys Lys
    770                 775                 780

Glu Leu Ser Glu Val Glu Lys Ala Lys Ile Arg Gly Ser Tyr Leu Thr
785                 790                 795                 800

Val Thr Leu Gln Arg Pro Thr Lys Glu Leu His Gly Thr Ser Ile Val
                805                 810                 815

Pro Lys Leu Gln Ala Ile Thr Ala Ser Ser Ala Asn Leu Arg His Ser
                820                 825                 830

Pro Arg Val Leu Val Gln His Cys Pro Ala Arg Thr Pro Gln Arg Gly
    835                 840                 845

Asp Glu Glu Gly Leu Gly Gly Glu Glu Glu Glu Glu Glu Glu Glu
    850                 855                 860

Glu Glu Asp Asp Ser Ala Glu Glu Gly Gly Ala Ala Arg Leu Asn Gly
865                 870                 875                 880

Arg Gly Ser Trp Ala Gln Asp Gly Asp Glu Ser Trp Met Gln Arg Glu
                885                 890                 895

Val Trp Met Ser Val Phe Arg Tyr Leu Ser Arg Arg Glu Leu Cys Glu
            900                 905                 910

Cys Met Arg Val Cys Lys Thr Trp Tyr Lys Trp Cys Cys Asp Lys Arg
    915                 920                 925

Leu Trp Thr Lys Ile Asp Leu Ser Arg Cys Lys Ala Ile Val Pro Gln
    930                 935                 940

Ala Leu Ser Gly Ile Ile Lys Arg Gln Pro Val Ser Leu Asp Leu Ser
945                 950                 955                 960

Trp Thr Asn Ile Ser Lys Lys Gln Leu Thr Trp Leu Val Asn Arg Leu
            965                 970                 975

Pro Gly Leu Lys Asp Leu Leu Leu Ala Gly Cys Ser Trp Ser Ala Val
            980                 985                 990

Ser Ala Leu Ser Thr Ser Ser Cys Pro Leu Leu Arg Thr Leu Asp Leu
            995                 1000                1005

Arg Trp Ala Val Gly Ile Lys Asp Pro Gln Ile Arg Asp Leu Leu
        1010                1015                1020

Thr Pro Pro Ala Asp Lys Pro Gly Gln Asp Asn Arg Ser Lys Leu
        1025                1030                1035
```

```
Arg Asn Met Thr Asp Phe Arg Leu Ala Gly Leu Asp Ile Thr Asp
    1040                1045                1050

Ala Thr Leu Arg Leu Ile Ile Arg His Met Pro Leu Leu Ser Arg
    1055                1060                1065

Leu Asp Leu Ser His Cys Ser His Leu Thr Asp Gln Ser Ser Asn
    1070                1075                1080

Leu Leu Thr Ala Val Gly Ser Ser Thr Arg Tyr Ser Leu Thr Glu
    1085                1090                1095

Leu Asn Met Ala Gly Cys Asn Lys Leu Thr Asp Gln Thr Leu Ile
    1100                1105                1110

Tyr Leu Arg Arg Ile Ala Asn Val Thr Leu Ile Asp Leu Arg Gly
    1115                1120                1125

Cys Lys Gln Ile Thr Arg Lys Ala Cys Glu His Phe Ile Ser Asp
    1130                1135                1140

Leu Ser Ile Asn Ser Leu Tyr Cys Leu Ser Asp Glu Lys Leu Ile
    1145                1150                1155

Gln Lys Ile Ser
    1160

<210> SEQ ID NO 8
<211> LENGTH: 1309
<212> TYPE: PRT
<213> ORGANISM: Mus musculus

<400> SEQUENCE: 8

Met Glu Ala Glu Lys Asp Ser Gly Arg Arg Leu Arg Ala Ile Asp Arg
1               5                   10                  15

Gln Arg Tyr Asp Glu Asn Glu Asp Leu Ser Asp Val Glu Glu Ile Val
            20                  25                  30

Ser Val Arg Gly Phe Ser Leu Glu Lys Leu Arg Ser Gln Leu Tyr
        35                  40                  45

Gln Gly Asp Phe Val His Ala Met Glu Gly Lys Asp Phe Asn Tyr Glu
    50                  55                  60

Tyr Val Gln Arg Glu Ala Leu Arg Val Pro Leu Val Phe Arg Asp Lys
65                  70                  75                  80

Asp Gly Leu Gly Ile Lys Met Pro Asp Pro Asp Phe Thr Val Arg Asp
                85                  90                  95

Val Lys Leu Leu Val Gly Ser Arg Arg Leu Val Asp Val Met Asp Val
            100                 105                 110

Asn Thr Gln Lys Gly Thr Glu Met Ser Met Ser Gln Phe Val Arg Tyr
        115                 120                 125

Tyr Glu Thr Pro Glu Ala Gln Arg Asp Lys Leu Tyr Asn Val Ile Ser
    130                 135                 140

Leu Glu Phe Ser His Thr Lys Leu Glu His Leu Val Lys Arg Pro Thr
145                 150                 155                 160

Val Val Asp Leu Val Asp Trp Val Asp Asn Met Trp Pro Gln His Leu
                165                 170                 175

Lys Glu Lys Gln Thr Glu Ala Thr Asn Ala Leu Ala Glu Met Lys Tyr
            180                 185                 190

Pro Lys Val Lys Lys Tyr Cys Leu Met Ser Val Lys Gly Cys Phe Thr
        195                 200                 205

Asp Phe His Ile Asp Phe Gly Gly Thr Ser Val Trp Tyr His Val Phe
    210                 215                 220

Arg Gly Gly Lys Ile Phe Trp Leu Ile Pro Pro Thr Leu His Asn Leu
225                 230                 235                 240
```

```
Ala Leu Tyr Glu Glu Trp Val Leu Ser Gly Lys Gln Ser Asp Ile Phe
            245                 250                 255
Leu Gly Asp Arg Val Glu Arg Cys Gln Arg Ile Glu Leu Lys Gln Gly
        260                 265                 270
Tyr Thr Phe Phe Ile Pro Ser Gly Trp Ile His Ala Val Tyr Thr Pro
    275                 280                 285
Val Asp Ser Leu Val Phe Gly Gly Asn Ile Leu His Ser Phe Asn Val
290                 295                 300
Pro Met Gln Leu Arg Ile Tyr Glu Ile Glu Asp Arg Thr Arg Val Gln
305                 310                 315                 320
Pro Lys Phe Arg Tyr Pro Phe Tyr Tyr Glu Met Cys Trp Tyr Val Leu
            325                 330                 335
Glu Arg Tyr Val Tyr Cys Val Thr Gln Arg Ser Tyr Leu Thr Gln Glu
            340                 345                 350
Tyr Gln Arg Glu Leu Met Leu Ile Asp Ala Pro Arg Lys Thr Ser Val
        355                 360                 365
Asp Gly Phe Ser Ser Asp Ser Trp Leu Asp Met Glu Glu Glu Ser Cys
    370                 375                 380
Glu Gln Gln Pro Gln Glu Glu Glu Glu Glu Asp Lys Glu Glu
385                 390                 395                 400
Glu Gly Asp Gly Ala Asp Lys Thr Pro Lys Pro Pro Thr Asp Pro
            405                 410                 415
Thr Ser Pro Thr Ser Thr Pro Pro Glu Asp Gln Asp Ser Thr Gly Lys
            420                 425                 430
Lys Pro Lys Ala Pro Ala Ile Arg Phe Leu Lys Arg Thr Leu Ser Asn
            435                 440                 445
Glu Ser Glu Glu Ser Val Lys Ser Thr Ser Met Pro Thr Asp Pro
450                 455                 460
Lys Thr Pro Thr Gly Ser Pro Ala Thr Glu Val Ser Thr Lys Trp Thr
465                 470                 475                 480
His Leu Thr Glu Phe Glu Leu Lys Gly Leu Lys Ala Leu Val Glu Lys
            485                 490                 495
Leu Glu Ser Leu Pro Glu Asn Lys Lys Cys Val Pro Glu Gly Ile Glu
            500                 505                 510
Asp Pro Gln Ala Leu Leu Glu Gly Val Lys Asn Val Leu Lys Glu His
            515                 520                 525
Val Asp Asp Asp Pro Thr Leu Ala Ile Thr Gly Val Pro Val Val Ser
    530                 535                 540
Trp Pro Lys Lys Thr Ala Lys Asn Arg Val Val Gly Arg Pro Lys Gly
545                 550                 555                 560
Lys Leu Gly Pro Ala Ser Ala Val Lys Leu Ala Ala Asn Arg Thr Thr
            565                 570                 575
Ala Gly Ala Arg Arg Arg Thr Arg Cys Arg Lys Cys Glu Ala Cys
        580                 585                 590
Leu Arg Thr Glu Cys Gly Glu Cys His Phe Cys Lys Asp Met Lys Lys
    595                 600                 605
Phe Gly Gly Pro Gly Arg Met Lys Gln Ser Cys Ile Met Arg Gln Cys
    610                 615                 620
Ile Ala Pro Val Leu Pro His Thr Ala Val Cys Leu Val Cys Gly Glu
625                 630                 635                 640
Ala Gly Lys Glu Asp Thr Val Glu Glu Glu Gly Lys Phe Asn Leu
            645                 650                 655
```

```
Met Leu Met Glu Cys Ser Ile Cys Asn Glu Ile Ile His Pro Gly Cys
            660                 665                 670

Leu Lys Ile Lys Glu Ser Glu Gly Val Val Asn Asp Glu Leu Pro Asn
        675                 680                 685

Cys Trp Glu Cys Pro Lys Cys Asn His Ala Gly Lys Thr Gly Lys Gln
    690                 695                 700

Lys Arg Gly Pro Gly Phe Lys Tyr Ala Ser Asn Leu Pro Gly Ser Leu
705                 710                 715                 720

Leu Lys Glu Gln Lys Met Asn Arg Asp Asn Lys Glu Gly Gln Glu Pro
            725                 730                 735

Ala Lys Arg Arg Ser Glu Cys Glu Glu Ala Pro Arg Arg Ser Asp
        740                 745                 750

Glu His Pro Lys Lys Val Pro Ala Asp Gly Ile Leu Arg Arg Lys Ser
        755                 760                 765

Asp Asp Val His Leu Arg Arg Lys Arg Lys Tyr Glu Lys Pro Gln Glu
        770                 775                 780

Leu Ser Gly Arg Lys Arg Ala Ser Ser Leu Gln Thr Ser Pro Gly Ser
785                 790                 795                 800

Ser Ser His Leu Ser Pro Arg Pro Leu Gly Ser Ser Leu Ser Pro
            805                 810                 815

Trp Trp Arg Ser Ser Leu Thr Tyr Phe Gln Gln Gln Leu Lys Pro Gly
            820                 825                 830

Lys Glu Asp Lys Leu Phe Arg Lys Arg Arg Ser Trp Lys Asn Ala
            835                 840                 845

Glu Asp Arg Leu Ser Leu Ala Asn Lys Pro Leu Arg Arg Phe Lys Gln
850                 855                 860

Glu Pro Glu Asp Asp Leu Pro Glu Ala Pro Lys Thr Arg Glu Ser
865                 870                 875                 880

Asp Gln Ser Arg Ser Ser Ser Pro Thr Ala Gly Pro Ser Thr Glu Gly
            885                 890                 895

Ala Glu Gly Pro Glu Glu Lys Lys Lys Val Lys Met Arg Arg Lys Arg
            900                 905                 910

Arg Leu Val Asn Lys Glu Leu Ser Lys Glu Leu Ser Lys Glu Leu Asn
            915                 920                 925

His Glu Ile Gln Lys Thr Glu Ser Thr Leu Ala His Glu Ser Gln Gln
            930                 935                 940

Pro Ile Lys Ser Glu Pro Glu Ser Glu Asn Asp Glu Pro Lys Arg Pro
945                 950                 955                 960

Leu Ser His Cys Glu Arg Pro His Arg Phe Ser Lys Gly Leu Asn Gly
            965                 970                 975

Thr Pro Arg Glu Leu Arg His Ser Leu Gly Pro Gly Leu Arg Ser Pro
            980                 985                 990

Pro Arg Val Met Ser Arg Pro Pro Ser Ala Ser Pro Pro Lys Cys
        995                 1000                1005

Ile Gln Met Glu Arg His Val Ile Arg Pro Pro Ile Ser Pro
    1010                1015                1020

Pro Pro Asp Ser Leu Pro Leu Asp Asp Gly Ala Ala His Val Met
        1025                1030                1035

His Arg Glu Val Trp Met Ala Val Phe Ser Tyr Leu Ser His Arg
        1040                1045                1050

Asp Leu Cys Val Cys Met Arg Val Cys Arg Thr Trp Asn Arg Trp
        1055                1060                1065

Cys Cys Asp Lys Arg Leu Trp Thr Arg Ile Asp Leu Asn Arg Cys
```

-continued

```
              1070              1075              1080
Lys Ser Ile Thr Pro Leu Met Leu Ser Gly Ile Ile Arg Arg Gln
        1085              1090              1095

Pro Val Ser Leu Asp Leu Ser Trp Thr Asn Ile Ser Lys Lys Gln
        1100              1105              1110

Leu Ser Trp Leu Ile Asn Arg Leu Pro Gly Leu Arg Asp Leu Val
        1115              1120              1125

Leu Ser Gly Cys Ser Trp Ile Ala Val Ser Ala Leu Cys Ser Ser
        1130              1135              1140

Ser Cys Pro Leu Leu Arg Thr Leu Asp Val Gln Trp Val Glu Gly
        1145              1150              1155

Leu Lys Asp Ala Gln Met Arg Asp Leu Leu Ser Pro Pro Thr Asp
        1160              1165              1170

Asn Arg Pro Gly Gln Met Asp Asn Arg Ser Lys Leu Arg Asn Ile
        1175              1180              1185

Val Glu Leu Arg Leu Ala Gly Leu Asp Ile Thr Asp Val Ser Leu
        1190              1195              1200

Arg Leu Ile Ile Arg His Met Pro Leu Leu Ser Lys Leu Gln Leu
        1205              1210              1215

Ser Tyr Cys Asn His Ile Asn Asp Gln Ser Ile Asn Leu Leu Thr
        1220              1225              1230

Ala Val Gly Thr Thr Thr Arg Asp Ser Leu Thr Glu Val Asn Leu
        1235              1240              1245

Ser Asp Cys Asn Lys Val Thr Asp Leu Cys Leu Ser Phe Phe Lys
        1250              1255              1260

Arg Cys Gly Asn Ile Cys His Ile Asp Leu Arg Tyr Cys Lys Gln
        1265              1270              1275

Val Thr Lys Glu Gly Cys Glu Gln Phe Ile Ala Glu Met Ser Val
        1280              1285              1290

Ser Val Gln Phe Gly Gln Val Glu Glu Lys Leu Leu Gln Lys Leu
        1295              1300              1305

Ser
```